(12) United States Patent
Walters et al.

(10) Patent No.: US 7,655,323 B2
(45) Date of Patent: *Feb. 2, 2010

(54) OLEDS UTILIZING MACROCYCLIC LIGAND SYSTEMS

(75) Inventors: Robert Walters, Export, PA (US); Peter B. Mackenzie, Murrysville, PA (US); Mark E. Thompson, Anaheim Hills, CA (US)

(73) Assignees: The University of Southern California, Los Angeles, CA (US); Universal Display Corporation, Ewing, NJ (US)

( * ) Notice: Subject to any disclaimer, the term of this patent is extended or adjusted under 35 U.S.C. 154(b) by 516 days.

This patent is subject to a terminal disclaimer.

(21) Appl. No.: 11/031,078

(22) Filed: Jan. 10, 2005

(65) Prior Publication Data

US 2005/0260445 A1 Nov. 24, 2005

Related U.S. Application Data

(63) Continuation-in-part of application No. 10/880,384, filed on Jun. 28, 2004, now Pat. No. 7,393,599, which is a continuation-in-part of application No. 10/849,301, filed on May 18, 2004, now Pat. No. 7,491,823.

(51) Int. Cl.
H01L 51/54 (2006.01)
(52) U.S. Cl. ............ 428/690; 428/917; 313/504; 257/E51.044
(58) Field of Classification Search .................. None
See application file for complete search history.

(56) References Cited

U.S. PATENT DOCUMENTS

| | | | |
|---|---|---|---|
| 4,769,292 A | 9/1988 | Tang et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,160,267 A * | 12/2000 | Kunugi et al. | 257/40 |
| 6,294,398 B1 | 9/2001 | Kim et al. | |
| 6,303,238 B1 | 10/2001 | Thompson et al. | |
| 6,310,360 B1 | 10/2001 | Forrest et al. | |
| 6,337,102 B1 | 1/2002 | Forrest et al. | |
| 6,383,666 B1 | 5/2002 | Kim et al. | |
| 6,420,057 B1 | 7/2002 | Ueda et al. | |
| 6,458,475 B1 | 10/2002 | Adachi et al. | |
| 6,468,819 B1 | 10/2002 | Kim et al. | |
| 6,548,956 B2 | 4/2003 | Forrest et al. | |
| 6,576,134 B1 | 6/2003 | Agner | |
| 6,602,540 B2 | 8/2003 | Gu et al. | |
| 6,734,457 B2 | 5/2004 | Yamazaki et al. | |
| 6,824,895 B1 | 11/2004 | Sowinski et al. | |
| 7,154,114 B2 * | 12/2006 | Brooks et al. | 257/40 |
| 7,279,704 B2 * | 10/2007 | Walters et al. | 257/40 |
| 7,393,599 B2 * | 7/2008 | Thompson et al. | 428/690 |
| 7,445,855 B2 * | 11/2008 | Mackenzie et al. | 428/690 |
| 2001/0015432 A1 | 8/2001 | Igarashi et al. | |
| 2001/0019782 A1 | 9/2001 | Igarashi et al. | |
| 2002/0024293 A1 | 2/2002 | Igarashi et al. | |
| 2002/0034656 A1 | 3/2002 | Thompson et al. | |
| 2002/0048689 A1 | 4/2002 | Igarashi et al. | |
| 2002/0063516 A1 | 5/2002 | Tsuboyama et al. | |
| 2002/0064681 A1 | 5/2002 | Takiguchi et al. | |
| 2002/0071963 A1 | 6/2002 | Fujii | |
| 2002/0121638 A1 | 9/2002 | Grushin et al. | |
| 2002/0182441 A1 | 12/2002 | Lamansky et al. | |
| 2002/0190250 A1 | 12/2002 | Grushin et al. | |
| 2003/0068526 A1 | 4/2003 | Kamatani et al. | |
| 2003/0068536 A1 | 4/2003 | Tsuboyama et al. | |
| 2003/0072964 A1 | 4/2003 | Kwong et al. | |
| 2003/0091862 A1 | 5/2003 | Tokito et al. | |
| 2003/0096138 A1 | 5/2003 | Lecloux et al. | |
| 2003/0141809 A1 | 7/2003 | Furugori et al. | |
| 2003/0162299 A1 | 8/2003 | Hsieh et al. | |
| 2003/0230980 A1 | 12/2003 | Forrest et al. | |
| 2004/0075096 A1 | 4/2004 | Grushin et al. | |
| 2004/0174116 A1 | 9/2004 | Lu et al. | |
| 2004/0209116 A1 | 10/2004 | Ren et al. | |
| 2005/0170206 A1 | 8/2005 | Ma et al. | |
| 2005/0260441 A1 | 11/2005 | Thompson et al. | |
| 2006/0258043 A1 | 11/2006 | Bold et al. | |

FOREIGN PATENT DOCUMENTS

| | | |
|---|---|---|
| EP | 1191613 | 3/2002 |
| EP | 1191614 | 3/2002 |
| EP | 1239526 | 9/2002 |
| WO | WO 92/02714 | 2/1992 |
| WO | WO 02/02714 | 1/2002 |

(Continued)

OTHER PUBLICATIONS

Baldo et al., "Highly Efficient Phosphorescent Emission from Organic Electroluminescent Devices," Nature, vol. 395, pp. 151-154 (1998).
Baldo et al., "Very High-Efficiency Green Organic Light-Emitting Devices Based on Electrophosphorescence," Appl. Phys. Lett., vol. 75, No. 1, pp. 4-6 (1999).
Adachi et al., "Nearly 100% Internal Phosphorescent Efficiency in an Organic Light Emitting Device," J. Appl. Phys., vol. 90, pp. 5048-5051 (2001).

(Continued)

Primary Examiner—Marie R. Yamnitzky
(74) Attorney, Agent, or Firm—Kenyon & Kenyon LLP

(57) ABSTRACT

The present invention provides organic light emitting devices (OLEDs) and materials with improved stability and efficiency when incorporated into an OLED. The materials include organometallic compounds having carbene atom/donor coordinated to a metal center. The compounds may be macrocyclic electrophosphors. The compounds may also include a macrocyclic ligand coordinated to a metal center.

28 Claims, 3 Drawing Sheets

FOREIGN PATENT DOCUMENTS

| | | |
|---|---|---|
| WO | WO 02/15645 | 2/2002 |
| WO | WO 02/074015 | 9/2002 |
| WO | WO 03/084972 | 10/2003 |
| WO | WO 03/088271 | 10/2003 |
| WO | WO 03/099959 | 12/2003 |
| WO | WO 2004/099339 | 11/2004 |
| WO | WO 2004/108857 | 12/2004 |

OTHER PUBLICATIONS

Koizumi et al, "Terpyridine-Analogous (N,N,C)-Tridentate Ligands: Synthesis, Structures, and Electrochemical Properties of Ruthenium (II) Complexes Bearing Tridentate Pyridinium and Pyridinylidene Ligands," Organometallics, vol. 22, pp. 970-975 (2003).

Ashkenazi et al., "Discovery of the First Metallaquinone," J. Am. Chem. Soc., vol. 122, pp. 8797-8798 (2000).

Cattoen, et al., "Amino-Aryl-Carbenes: Alternative Ligands for Transition Metals?" J. Am. Chem. Soc., vol. 126, pp. 1342-1343 (2004).

Wong et al., "Ruthenium (II) o-Acetylide and Carbene Complexes Supported by the Terpyridine-Bipyridine Ligand Set: Structural, Spectroscopic, and Photochemical Studies," Organometallics, vol. 23, pp. 2263-2272 (2004).

Klapars et al., "A General and Efficient Copper Catalyst for the Amidation of Aryl Halides and the N-Arylation of Nitrogen Heterocycles," J. Am. Chem. Soc., vol. 123, pp. 7727-7729 (2001).

Bourissou et al., "Stable Carbenes," Chem Rev. vol. 100, pp. 39-91 (2000).

Lai et al., "Carbene and Isocyanide Ligation at Luminescent Cyclometalated 6-Phenyl-2,2'-bipyridyl Platinum (II) Complexes: Structural and Spectroscopic Studies," Organometallics, vol. 18, pp. 3327-3336 (1999).

Xue et al., "Spectroscopic and Excited-State Properties of Luminescent Rhenium (I) N-Heterocyclic Carbene Complexes Containing Aromatic Diimine Ligands," Organometallics, vol. 17, pp. 1622-1630 (1998).

Wang et al., "Facile Synthesis of Silver (I)-Carbene Complexes. Useful Carbene Transfer Agents," Organometallics, vol. 17, pp. 972-975 (1998).

Cardin et al., "Transition Metal-Carbene Complexes," Chem. Rev., vol. 72, pp. 545-574 (1972).

Kunkley et al., "Optical Properties of Transition Metal Complexes with N-Heterocyclic Carbenes as Ligands. 1,3-di-t-Butylimidazol-2-ylidene as Charge Transfer Donor and Acceptor," J. Organometallic Chem., vol. 684, pp. 113-116 (2003).

Anthony R. Chianese et al., "Abnormal C5-Bound N-Heterocyclic Carbenes: Extremely Strong Electron Donor Ligands and Their Iridium (I) and Iridium (III) Complexes," Organometallics, vol. 23, pp. 2461-2468 (2004).

Xile Hu et al., "Group 11 Metal Complexes of N-Heterocyclic Carbene Ligands: Nature of the Metal-Carbene Bond," Organometallics, vol. 23, pp. 755-764 (2004).

Xile Hu et al., "A Bis-Carbenealkenyl Copper(I) Complex from a Tripodal Tris-Carbene Ligand," Organometallics, vol. 22, pp. 3016-3018 (2003).

Siu-Wai Lai et al., "[{Pt(CN)($C_{10}H_{21}N_4$)}$_6$]: A Luminescent Hexanuclear Platinum (II) Macrocycle Containing Chelating Dicarbene and Bridging Cyanide Ligands," Angew. Chem. Int. Ed., vol. 37, No. 1/2, pp. 182-184 (1998).

Xile Hu et al., "Silver Complexes of a Novel Tripodal N-Heterocyclic Carbene Ligand: Evidence for Significant Metal-Carbene π-Interaction," Organometallics, vol. 22, pp. 612-614 (2003).

James P. Collman et al., "Principles and Applications of Organotransition Metal Chemistry," University Science Books, Mill Valley, CA, pp. 119-121(1987).

Thomas H. Lowry et al., "Mechanism and Theory in Organic Chemistry," Harper & Row Publishers, New York, p. 256 (1976).

Nemcsok et al., "The Significance of π Interactions in Group 11 Complexes with N-Heterocyclic Carbenes", Organometallics, vol. 23, pp. 3640-3646, 2004.

Nicholas J. Turro, Modern Molecular Photochemistry, University Science Books, Sausalito, California, pp. 109-110.

"Inorganic Chemistry" ($2^{nd}$ Edition) by Gary L. Miessler and Donald A. Tarr, Prentice Hall, pp. 1-3, 422-424, 369-397, Aug. 1999 version.

Jason Brooks et al., "Synthesis and Characterization of Phosphorescent Cyclometallated Platinum-Complexes," Inorganic Chemistry 41(12), 3055-3066 (2002).

Arnold Tamayo et al., "Synthesis and Characterization of Facial and Meridional Tris-cyclometallated Iridium (III) Complexes," Journal of the American Chemical Society 125(24), 7377-7387 (2003).

Jay C. Amicangelo, "Theoretical study of a photochromic platinum complex using density functional theory methods," Abstracts of Papers, 228th ACS National Meeting, Philadelphia, PA, United States, Aug. 22-26, 2004.

Alessandro Marrone et al., "Metal Fragment Modulation of Metallacumulene Complexes: A Density Functional Study," Organometallics 23(21), 4952-4963 (2004).

Irina Diaz-Acosta et al., "Calculated and experimental geometries and infrared spectra of metal tris-acetylacetonates: vibrational spectroscopy as a probe of molecular structure for ionic complexes, Part II", Spectrochimica acta, Part A: Molecular and biomolecular spectroscopy, 59(2), 363-377 (Jan. 15, 2003).

S. Strauss et al., "The Search for Larger and More Weakly Coordinating Anions", Chem. Rev., 1993, 93, pp. 927-642.

Adachi et al., "High-efficiency organic electrophosphorescent devices with tris (2-phenylpyridine) iridium doped into electron-transporting materials", Applied Physics Letters, vol. 77, No. 6, pp. 904-906, Aug. 7, 2000.

Martin Pope and Charles E. Swenberg, Electronic Processes in Organic Crystals and Polymers, Second Edition, Oxford Science Publications, p. 207.

<http://chimge.unil.ch/En/complexes/1cpx23.htm>, The formation of complexes, printed May 24, 2005.

<http://www.wordiq.com/definition/Porphyrin>, wordiq.com, Definition of porphyrin, printed May 24, 2005.

F. Albert Cotton, et al., Advanced Inorganic Chemistry, John Wiley & Sons, Inc., New York, 1999, pp. 29-30.

S. Lamansky, et al., "Highly Phosphorescent Bis-Cyclometalated Iridium Complexes: Synthesis, Photophysical Characterization, and Use in Organic Light Emitting Diodes", J. Am. Chem. Soc., 2001, 123, pp. 4304-4312.

R.J. Holmes, et al., "Efficient, deep-blue organic electrophosphorescence by guest charge trapping", Applied Physics Letters, vol. 83, No. 18, pp. 3818-3820, Nov. 3, 2003.

Nicholas A. Piro, et al., "Pyridinium-derived N-heterocyclic carbene ligands: syntheses, structures and reactivity of N-(2'-pyridyl)pyridin-2-ylidene complexes of nickel(II), palladium(II) and platinum(II)", Polyhedron 23 (2004), pp. 2797-2804.

Take-aki Koizumi, et al., "Synthesis and electrochemical properties of bis(bipyridine)ruthenium(II) complexes bearing pyridinyl- and pyridinylidene ligands induced by cyclometalation of N'-methylated bipyridium analogs", Journal of Organometallic Chemistry, vol. 690, Issue 5, Mar. 2005, pp. 1258-1264.

U.S. Appl. No. 10/233,470, to Shtein et al., filed Sep. 4, 2002, (not published).

U.S. Appl. No. 60/370,676, filed Apr. 2002.

Hitchcock et al., Synthesis of Homoleptic Tris(Organo-Chelate)Iridium(III) Complexes By Spontaneous ortho-Metallation of Electron-Rich Olefin-Derived N,N'Diarylcarbene Ligands and The X-Ray Structures of Fac-[Ir{CN($C_6H_4$Me-p)($CH_2$)$_2$N$C_6H_3$Me-p}3 and mer-[Ir-{CN($C_6H_4$-Me-p)($CH_2$)$_2$N$C_6H_3$Me-p}2{CN($C_6H_4$Me-p)($CH_2$)$_2$N$C_6H_4$Me-p}](A Product of of HCl Cleavage), J. of Organometallic Chemistry, 239(1982); C26-C30.

Grundemann et al., Abnormal Ligand Binding and Reversible Ring Hydrogenation in the Reaction of Imidazolium Salts with Ir$H_5$(PP$h_3$)$_2$, J. Am. Chem. Soc., 124 (2002), pp. 10473-10481.

* cited by examiner

Figure 3: Room Temperature Emission Spectrum
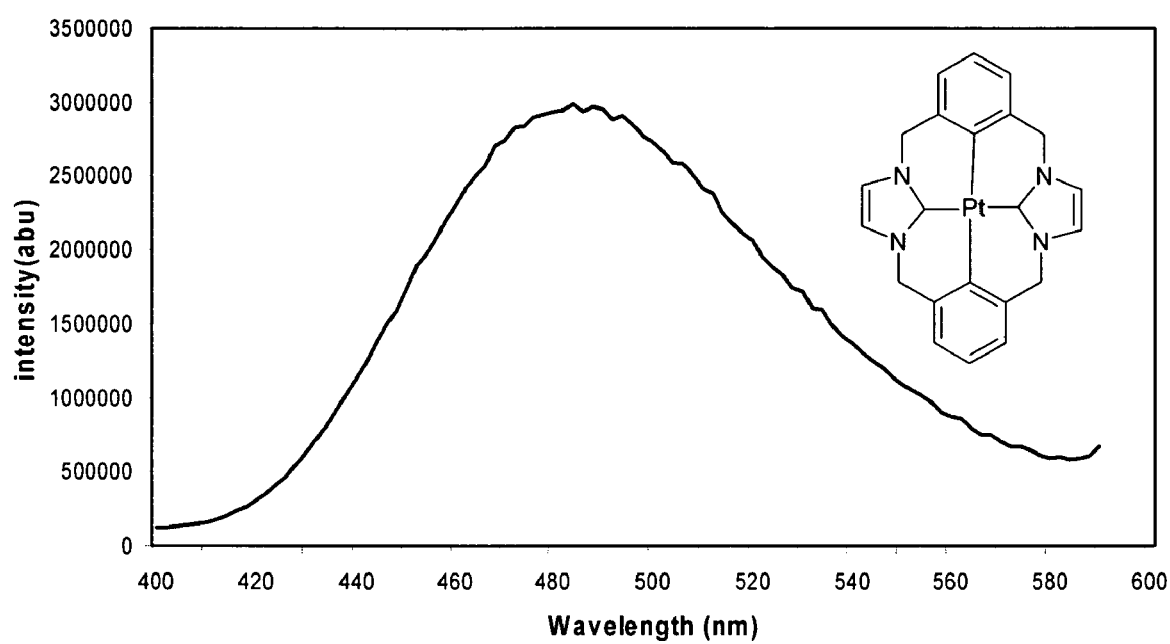

OLEDS UTILIZING MACROCYCLIC LIGAND SYSTEMS

CROSS-REFERENCE TO RELATED APPLICATIONS

This application is a continuation-in-part of U.S. application Ser. No. 10/880,384, filed Jun. 28, 2004, now U.S. Pat. No. 7,393,599, which is a continuation-in-part of U.S. application Ser. No. 10/849,301, filed May 18, 2004, now U.S. Pat. No. 7,491,823, each of which is incorporated by reference in its entirety.

RESEARCH AGREEMENTS

The claimed invention was made by, on behalf of, and/or in connection with one or more of the following parties to a joint university corporation research agreement: Princeton University, The University of Southern California and Universal Display Corporation. The agreement was in effect on and before the date the claimed invention was made, and the claimed invention was made as a result of activities undertaken within the scope of the agreement.

FIELD OF THE INVENTION

The present invention relates to efficient organic light emitting devices (OLEDs), and more specifically to organic materials used in such devices. More specifically, the present invention relates to phosphorescent emitting materials with improved stability and efficiency when incorporated into an OLED.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well defined chemical formula with a single molecular weight, whereas a polymer has a chemical formula and a molecular weight that may vary from molecule to molecule. As used herein, "organic" includes metal complexes of hydrocarbyl and heteroatom-substituted hydrocarbyl ligands.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

Industry standards call for the lifetime of full color displays to be at least about 5000 hours. In addition, high stability and efficiency are important characteristics of high quality displays. These requirements have helped generate a need for materials that exhibit longer lifetimes, higher stability, and higher efficiency than have been generally achieved by devices using many prior art compounds.

SUMMARY OF THE INVENTION

The present invention provides an organic light emitting device that has an anode, a cathode, and one or more organic layers between the anode and the cathode. The present invention also provides materials having improved stability for use in an OLED. In some embodiments, the materials are macrocyclic electrophosphors.

In one embodiment, the organic layer comprises an organometallic compound further comprising a macrocyclic ligand coordinated to a metal center. In one embodiment, the macrocyclic ligand is planar. In another embodiment, the macrocyclic ligand is a tetradentate ligand. In another embodiment, the macrocyclic tetradentate ligand comprises two 5-membered rings and two 6-membered rings, each coordinated to the metal center.

In one embodiment, the present invention provides an OLED, wherein the organic layer comprises a macrocyclic compound of structure I:

wherein

M is a metal;

A is C or N;

$Z_1$ is C or N;

$R^1$, $R^2$, $R^3$, and $R^4$ are independently H, alkyl, alkenyl, alkynyl, heteroalkyl, aralkyl, aryl, heteroaryl, C(O)R', C(O)OR', or C(O)NR'$_2$; and each of $R^1$ and $R^2$, $R^2$ and $R^3$, and $R^3$ and $R^4$ independently and optionally can form a 5- or 6-member cyclic group, wherein said cyclic group is cycloalkyl, cycloheteroalkyl, aryl, or heteroaryl; and wherein said cyclic group is optionally substituted by one or more substituents J;

each substituent J is independently R', O—R', N(R')$_2$, SR', C(O)R', C(O)OR', C(O)NR'$_2$, CN, CF$_3$, NO$_2$, SO$_2$, SOR', SO$_3$R', or halo, and any two J groups on adjacent ring atoms can optionally form a 5- or 6-member cyclic group;

each R' is independently H, alkyl, alkenyl, alkynyl, heteroalkyl, aralkyl, aryl, or heteroaryl;

Q is an ancillary ligand;

n is a value from 2 to the maximum number of ligands that may be attached to metal M;

m+n is the maximum number of ligands that may be attached to metal M.

In one embodiment, M is Ir, Pt, Pd, Rh, Re, Ru, Os, Tl, Pb, Bi, In, Sn, Sb, Te, Au, or Ag. In one preferred embodiment, M is Pt.

In one embodiment, n is 2 and m is 0. The present invention provides specific exemplary compounds.

In one embodiment, the compound further comprises a carbene donor. The present invention provides specific exemplary carbene compounds.

In one embodiment, the present invention provides a tetradentate compound having a structure II:

wherein

M is a metal;

A is C or N;

$Z_1$ is C or N;

$R^1$, $R^2$, $R^3$, and $R^4$ are independently H, alkyl, alkenyl, alkynyl, heteroalkyl, aralkyl, aryl, heteroaryl, C(O)R', C(O)OR', or C(O)NR'$_2$; and each of $R^1$ and $R^2$, $R^2$ and $R^3$, and $R^3$ and $R^4$ independently and optionally can form a 5- or 6-member cyclic group, wherein said cyclic group is cycloalkyl, cycloheteroalkyl, aryl, or heteroaryl; and wherein said cyclic group is optionally substituted by one or more substituents J;

each substituent J is independently R', O—R', N(R')$_2$, SR', C(O)R', C(O)OR', C(O)NR'$_2$, CN, CF$_3$, NO$_2$, SO$_2$, SOR', SO$_3$R', or halo, and any two J groups on adjacent ring atoms can optionally form a 5- or 6-member cyclic group;

each R' is independently H, alkyl, alkenyl, alkynyl, heteroalkyl, aralkyl, aryl, or heteroaryl;

In one embodiment, the present invention provides a tetradentate compound having a structure III:

wherein

M is Pt or Pd;

$Z_2$ is C or Si; and the phenyl groups may be optionally substituted with one or more substituents J.

In one embodiment, the tetradentate compound has a structure IV:

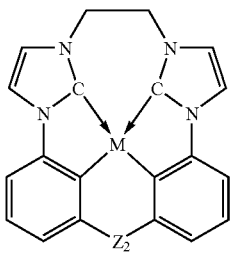

IV wherein

M is Pt or Pd;

$Z_2$ is C or Si; and the phenyl groups may be optionally substituted with one or more substituents J.

In another embodiment, the invention provides an organic light emitting device, comprising an anode, a cathode, and a phosphorescent emissive region disposed between the anode and the cathode, wherein the emissive region comprises an emissive material having the structure V:

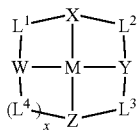

V wherein M is a metal; W, X, Y, and Z are independently a group containing C, N, P, O, or S coordinated to the metal M; and wherein at least one of W, X, Y, or Z is coordinated to the metal by a carbene donor. W, X, Y, and Z are linked to one another by linking groups $L^1$, $L^2$, $L^3$, and optionally $L^4$.

In a further embodiment, the emissive material has the structure VI:

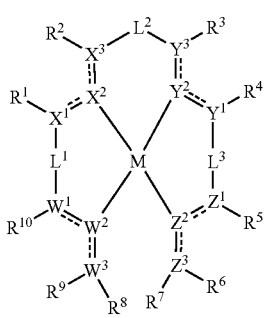

VI wherein:

M is Pt or Pd;

the dotted lines represent optional double bonds;

$W^1$, $W^3$, $X^1$, $X^3$, $Y^1$, $Y^3$, $Z^1$, and $Z^3$ are independently C or N;

$W^2$, $X^2$, $Y^2$, and $Z^2$ are independently C, N, O, S or P; wherein at least one of $W^2$, $X^2$, $Y^2$ and $Z^2$ is a carbene;

wherein for each group W, X, Y, and Z at least one of atoms 1, 2, and 3 is C;

$L^1$, $L^2$, and $L^3$ are independently a linking group;

$R^7$ and $R^8$ may optionally be joined to form a linking group $L^4$;

$R^{1-10}$ are independently H, alkyl, alkenyl, alkynyl, heteroalkyl, aralkyl, aryl, heteroaryl, C(O)R', C(O)OR', or C(O)NR'$_2$;

each of $R^1$ and $R^2$, $R^3$ and $R^4$, $R^5$ and $R^6$, and $R^9$ and $R^{10}$, taken together with the atoms of groups X, Y, Z, and W, respectively, can independently and optionally can form a 5- or 6-member cyclic group or an 8- to 10-membered fused bicyclic group, which may be optionally substituted by one or more substituents J;

each substituent J is independently R', O—R', N(R')$_2$, SR', C(O)R', C(O)OR', C(O)NR'$_2$, CN, CF$_3$, NO$_2$, SO$_2$, SOR', SO$_3$R', or halo, and any two J groups on adjacent ring atoms can optionally form a 5- or 6-member cyclic group; and each R' is independently H, alkyl, alkenyl, alkynyl, heteroalkyl, aralkyl, aryl, or heteroaryl.

In a preferred embodiment, the emissive material has the structure VII:

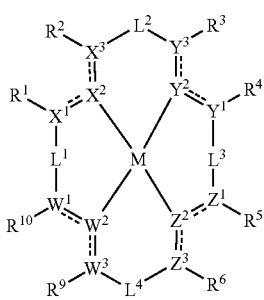

VII wherein $L^4$ is a linking group.

In a further preferred embodiment, the emissive material has the structure VIII:

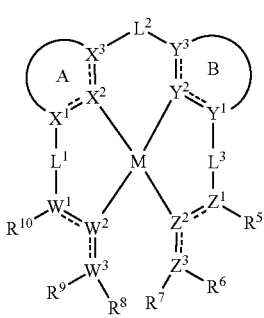

VIII wherein A and B are independently a 5- or 6-membered cyclic group or a 8- to 10-membered fused bicyclic group, which may be optionally substituted with one or more substituents J.

In a further preferred embodiment of structure VIII, the emissive material has the structure IX:

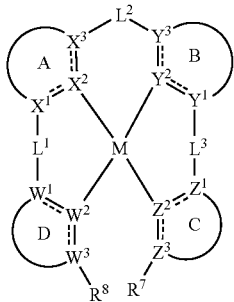

IX wherein A, B, C, and D are independently a 5- or 6-membered cyclic group or a 8- to 10-membered fused bicyclic group, which may be optionally substituted with one or more substituents J.

In a further preferred embodiment, the emissive material has the structure X:

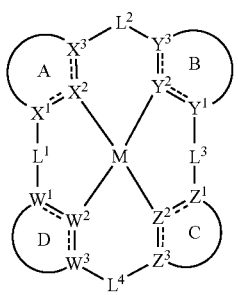

X wherein $L^4$ is a linking group.

In preferred embodiments, all of the rings A, B, C, and D are aromatic rings. In an especially preferred embodiment, two of the rings A, B, C, and D are imidazole rings, and each of the remaining two rings is a phenyl ring or a pyridyl ring.

In one embodiment, the emissive material has the structure XI:

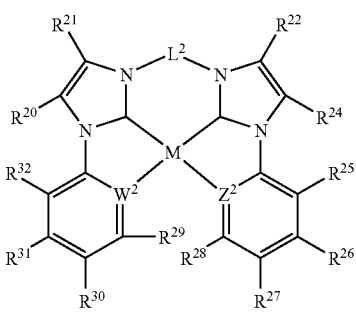

XI wherein:
$W^2$ and $Z^2$ are independently C or N;
$L^2$ is a linking group;

$R^{28}$ and $R^{29}$ may optionally be joined to form a linking group $L^4$;
$R^{20-32}$ are independently a substituent J.

In a preferred embodiment, the emissive material has the structure XII:

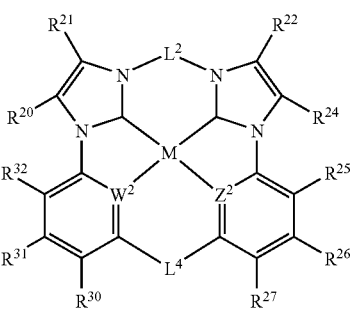

XII wherein $L^4$ is a linking group.

In a further embodiment of the invention, the emissive material has the structure XIII:

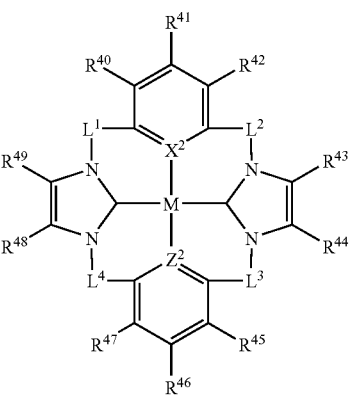

XIII wherein:
$X^2$ and $Z^2$ are independently C or N;
$L^1$, $L^2$, $L^3$, and $L^4$ are independently a linking group;
$R^{40-49}$ are independently a substituent J.

In another embodiment, the invention provides a device comprising an anode, a cathode, and an organic layer disposed between the anode and the cathode, the organic layer comprising a compound with one or more carbene atoms coordinated to a $d^8$ metal. Preferred metals for this embodiment include Pt(II), Pd(II), Ir(I), Au(III), or Rh(I). Most preferably, the metal is Pt(II).

In one embodiment, the metal is coordinated to one or more carbene donors; 0-3 neutral donors; and 0-3 monoanionic donors; wherein the total number of donors is the maximum number of ligands that may be attached to the metal, and wherein each donor is optionally linked to one or more adjacent donors. Exemplary donors are provided.

In a preferred embodiment, the donors are linked to form a macrocyclic ligand. In another preferred embodiment, the macrocyclic ligand is planar. In another preferred embodiment, the metal is coordinated to 4 donors, and the donors are linked to form a tetradentate ligand.

In one embodiment, the metal forms a carbon-metal bond with at least one carbon atom that is not a carbene donor. In a preferred embodiment, the metal forms a carbon metal bond with a phenyl group. In an especially preferred embodiment, the metal is coordinated to two carbene donors and two phenyl groups.

In one embodiment, the metal is coordinated to two bidentate ligands. In another embodiment, the metal is coordinated to one tridentate ligand and one monodentate ligand. In another embodiment, the metal is coordinated to a tetradentate ligand.

In a preferred embodiment, at least one ligand has a triplet energy corresponding to a wavelength of less than 450 nm.

Exemplary compounds are provided.

BRIEF DESCRIPTION OF THE DRAWINGS

FIG. 3 shows an exemplary room temperature emission spectrum.

DETAILED DESCRIPTION

Figure 1:
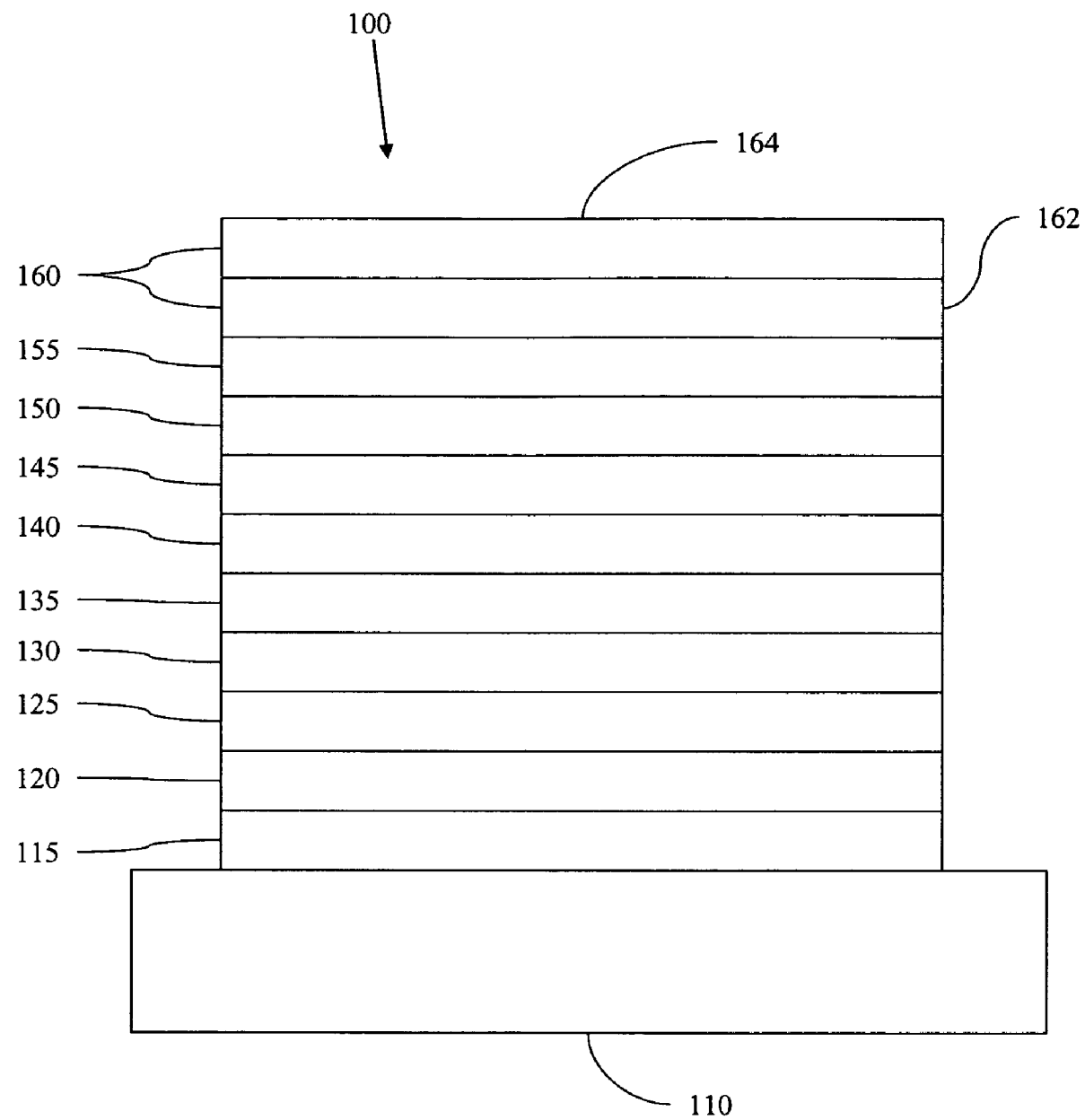
FIG. 1 shows an organic light emitting device having separate electron transport, hole transport, and emissive layers, as well as other layers.

The present invention provides an organic light emitting device that has an anode, a cathode, and one or more organic layers between the anode and the cathode. The present invention also provides materials having improved stability for use in an OLED. In some embodiments, the materials are macrocyclic electrophosphors. By linking individual ligands together to form a multidentate ligand system, it is possible to increase the stability of the metal complexes formed using the ligands. In one embodiment, the device has an emissive layer comprising an emissive material which is a phosphorescent organometallic emissive material. Previously used phosphorescent emissive materials, such as $Ir(ppy)_3$, use individual bidentate ligands. The phosphorescent emissive material in the present invention is composed of a heavy metal atom and a multidentate ligand system formed by linking ligands.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that a material that exhibits phosphorescence at liquid nitrogen temperatures may not exhibit phosphorescence at room temperature. But, as demonstrated by Baldo, this problem may be addressed by selecting phosphorescent compounds that do phosphoresce at room temperature. Representative emissive layers include doped or un doped phosphorescent organometallic materials such as disclosed in U.S. Pat. Nos. 6,303,238 and 6,310,360; U.S. Patent Application Publication Nos. 2002-0034656; 2002-0182441; 2003-0072964; and WO 02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak The term "organometallic" as used herein is as generally understood by one of ordinary skill in the art and as given, for example, in "Inorganic Chemistry" (2nd Edition) by Gary L. Miessler and Donald A. Tarr, Prentice-Hall (1998). Thus, the term organometallic refers to compounds which have an organic group bonded to a metal through a carbon-metal bond. This class does not include per se coordination compounds, which are substances having only donor bonds from heteroatoms, such as metal complexes of amines, halides, pseudohalides (CN, etc.), and the like. In practice organometallic compounds generally comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN or CO.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in U.S. patent application Ser. No. 10/173,682 to Forrest et al. (now abandoned; Pub. No. US 2003/0230980 A1), which is incorporated by reference in its entirety. Other hole transport layers may be used.

Emissive layer 135 comprises an organic dopant material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material. The host material may be capable of transporting electrons and/or holes, and is doped with the emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of fluorescent emissive materials include DCM and DMQA. Examples of host materials include $Alq_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecular emissive material may be present as the core of a dendrimer.

Electron transport layer 145 may include a material capable of transporting electrons. Electron transport layer 145 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in United States Patent Application Publication No. 2002-0071963 A1 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2, and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2002-0071963 A1 to Forrest et al., which are incorporated by reference in their entireties.

As used herein, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 Lu et al., now U.S. Pat. No. 7,071,615, which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., now U.S. Pat. No. 7,071,615, which is incorporated by reference in its entirety.

Figure 2:
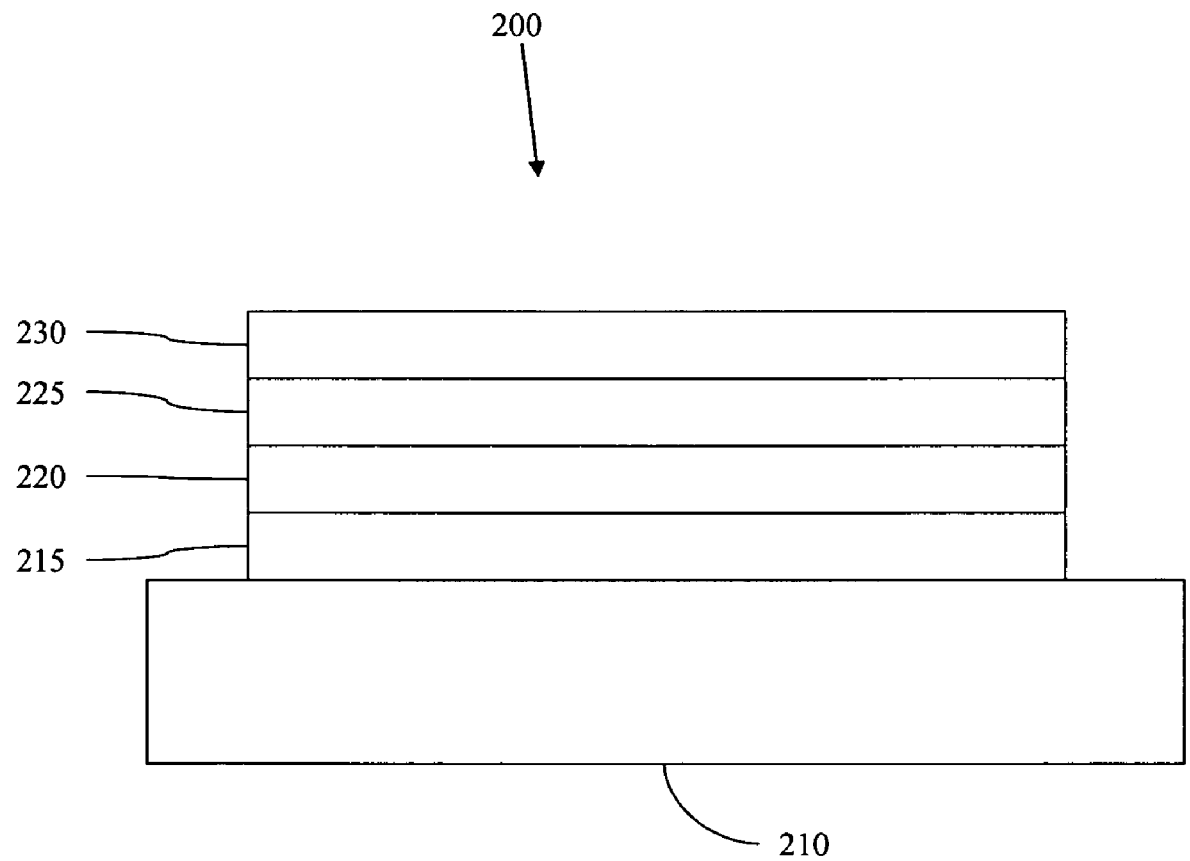
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the emissive materials are macrocyclic electrophosphors. In these embodiments, the phosphorescent emissive material comprises a heavy metal atom and a multidentate ligand system, for example a tetradentate or hexadentate ligand system. By linking two or more ligands together to give a multidentate ligand system, it is possible to increase the stability of the metal complexes formed using the ligands.

In some embodiments, the donor atoms are members of a ring. The most stable complexes are formed when the internal diameter of the ring corresponds to the diameter of the cation.

In order to form a macrocyclic ligand, two or more ligands are linked to one another by a linking group. The linking group may be connected to each ligand by a covalent bond to any carbon or heteroatom of the ligand that does not interfere with the ligand's ability to bind to the metal. Linking groups include, for example, organic, organometallic, and other metal containing groups. Representative groups suitable for use as a linking group are bivalent and trivalent alkyl groups, aryl groups, silanes, ethers, and polyethers. In some embodiments, the ligands that are joined by a linking group are directly bonded to one another, in which case the term "linking group" is meant to refer to that bond.

In one embodiment, two bidentate ligands are linked by a single linking group. In another embodiment, two bidentate ligands are linked by two linking groups. The linking groups within the macrocyclic ligand can be the same or different from one another. In one embodiment, a tetradentate ligand comprises four linking groups, two of which comprise one or more linking atoms or heteroatoms and two of which are single bonds.

In one embodiment, the linking group provides no π-conjugation between the linked ligands. Having π-conjugation between the linked ligands may change the electronic properties of the ligands and the resulting metal complexes, such as a red-shift in the luminescence. It is desirable to link the ligands together to without significantly altering the electronic properties of the ligands and the resulting metal complex. A non-conjugated linking group may comprise at least one atom in the linkage, which contains no π-electrons, such as an sp$^3$ hybridized carbon or silicon.

In one embodiment, the compound comprising the macrocyclic ligand is organometallic.

In a preferred embodiment, the ligand is symmetrical across the metal center. Ligand symmetry may contribute to the stability of the macrocyclic ligand system.

In one embodiment, the ligand is a tetradentate ligand. When the tetradentate ligand comprises two identical bidentate ligands, the tetradentate ligand is "square."

In one embodiment, the tetradentate ligand comprises two 5-membered rings and two 6-membered rings, each ring coordinated to the metal center.

In one embodiment, the macrocyclic ligand is "planar." In the present invention, the ligand forms a plane defined by three atoms: two adjacent atoms each coordinated to the metal, and the metal atom itself. The planarity of a ligand can be determined by the angle between planes formed by the atoms coordinated to the metal, i.e., the interplanar angle. For instance, in formula V (described in further detail below), an interplanar angle exists between the plane of the coordinating atoms of W, X, and metal M and the plane of the coordinating atoms of Y, Z, and metal M. Likewise, an interplanar angle also exists between the plane of W, Z, and M and the plane of X, Y, and M.

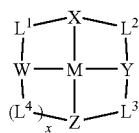

V

In the planar compounds of the present invention, each interplanar angle is less than about 15°. Preferably, each interplanar angle is less than about 10°, and most preferably, each interplanar angle is about 0°.

The best way to determine if a given metal complex is a planar macrocycle system is to determine its structure by x-ray crystallography. Absent a crystal structure, a theoretical calculation can be used to predict the degree of planarity. Energy minimized structures predicted using density functional theory (DFT) closely match those determined experimentally (by x-ray methods). Other calculation methods that give similar levels of correlation between theoretical and experimental structures can also be used. See, e.g., Jason Brooks et al., "Synthesis and Characterization of Phosphorescent Cyclometallated Platinum-Complexes," *Inorganic Chemistry* 41(12), 3055-3066 (2002); Arnold Tamayo et al., "Synthesis and Characterization of Facial and Meridional Tris-cyclometallated Iridium (III) Complexes," *Journal of the American Chemical Society* 125(24), 7377-7387 (2003); Jay C. Amicangelo, "Theoretical study of a photochromic platinum complex using density functional theory methods," Abstracts of Papers, 228th ACS National Meeting, Philadelphia, Pa., United States, Aug. 22-26 (2004); Alessandro Marrone et al., "Metal Fragment Modulation of Metallacumulene Complexes: A Density Functional Study," *Organometallics* 23(21), 4952-4963 (2004); Irina Diaz-Acosta et al., "Calculated and experimental geometries and infrared spectra of metal tris-acetylacetonates: vibrational spectroscopy as a probe of molecular structure for ionic complexes, Part II: Spectrochimica acta, Part A: Molecular and biomolecular spectroscopy, 59(2), 363-77 (2003 Jan. 15).

Exemplary planar compounds include structures III and IV:

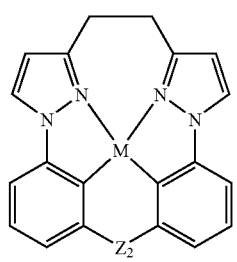

III

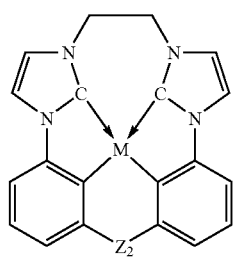

IV as well as other carbene compounds such as:

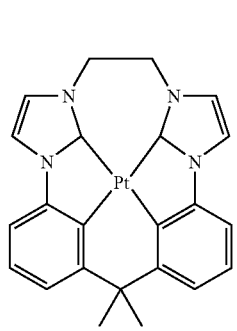 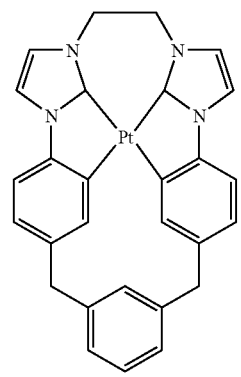

These compounds are described in further detail below.

In one embodiment, the compound of the present invention may be represented by a macrocyclic structure I:

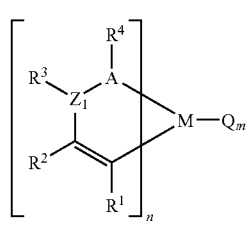

I wherein

M is a metal;

A is C or N;

$Z_1$ is C or N;

$R^1$, $R^2$, $R^3$, and $R^4$ are independently H, alkyl, alkenyl, alkynyl, heteroalkyl, aralkyl, aryl, heteroaryl, C(O)R', C(O)OR', or C(O)NR'$_2$; and each of $R^1$ and $R^2$, $R^2$ and $R^3$, and $R^3$ and $R^4$ independently and optionally can form a 5- or 6-member cyclic group, wherein said cyclic group is cycloalkyl, cycloheteroalkyl, aryl, or heteroaryl; and wherein said cyclic group is optionally substituted by one or more substituents J;

each substituent J is independently R', O—R', N(R')$_2$, SR', C(O)R', C(O)OR', C(O)NR'$_2$, CN, CF$_3$, NO$_2$, SO$_2$, SOR', SO$_3$R', or halo, and any two J groups on adjacent ring atoms can optionally form a 5- or 6-member cyclic group;

each R' is independently H, alkyl, alkenyl, alkynyl, heteroalkyl, aralkyl, aryl, or heteroaryl;

Q is an ancillary ligand;

n is a value from 2 to the maximum number of ligands that may be attached to metal M;

m+n is the maximum number of ligands that may be attached to metal M.

In some embodiments, the metal, M, is selected from the transition metals having an atomic weight greater than 40. Preferred metals for this embodiment include Ir, Pt, Pd, Rh, Re, Ru, Os, Tl, Pb, Bi, In, Sn, Sb, Te, Au, and Ag. More preferably, the metal is Pt or Pd. Most preferably, the metal is Pt.

Many embodiments of this invention comprise substituents J. Unless otherwise specified, each substituent J is independently R', O—R', N(R')$_2$, SR', C(O)R', C(O)OR', C(O)NR'$_2$, CN, CF$_3$, NO$_2$, SO$_2$, SOR', SO$_3$R', or halo, wherein any two J groups on adjacent ring atoms can optionally form a 5- or 6-member cyclic group; and wherein each R' is independently H, alkyl, alkenyl, alkynyl, heteroalkyl, aralkyl, aryl, or heteroaryl. Also, the possible cyclic groups formed by adjacent J groups may also be substituted by one or more substituents J.

Q is an optional ancillary ligand that may modify the photoactive properties of the molecule, for example by shifting the energy levels of a photoactive ligands, but it does not directly provide the energy levels involved in light emission.

In one embodiment, the present invention provides a tetradentate compound of structure I as described above. This embodiment is depicted as structure II:

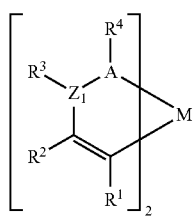

In this embodiment, two bidentate ligands are linked together by at least one linking group to form a tetradentate. The compounds of the present invention include structures IIa and IIb:

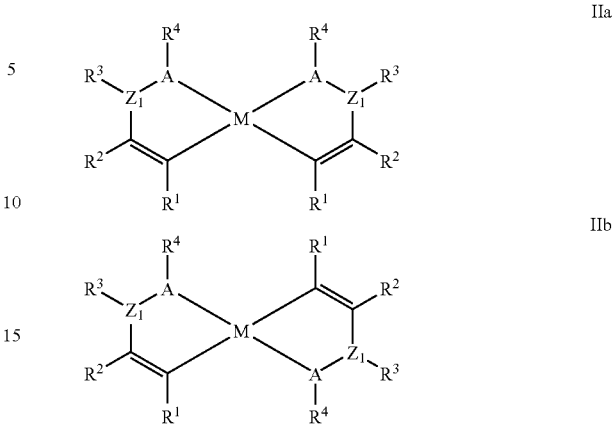

Each of structures IIa and IIb form a tetradentate when the two bidentate ligands are linked to one another by at least one linking group. For example, in structure IIa, the pair of $R^1$ groups can be linked together, the pair of $R^4$ groups can be linked together, or both pairs can be linked. Similarly, in structure IIb, one or both of the $R^1$ groups can be linked to its neighboring $R^4$ group.

The present invention also provides a compound having a structure III:

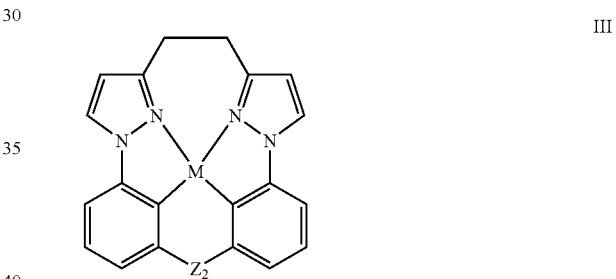

wherein

M is Pt or Pd;

$Z_2$ is C or Si; and the phenyl groups may be optionally substituted with one or more substituents J.

In another embodiment, the present invention provides a compound having a structure IV:

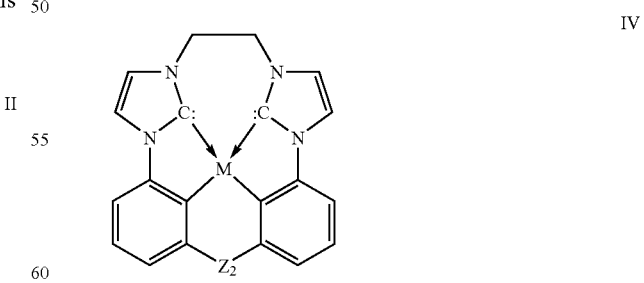

wherein

M is Pt or Pd;

$Z_2$ is C or Si; and the phenyl groups may be optionally substituted with one or more substituents J.

In some embodiments, the compound comprises a carbene donor. See U.S. Ser. No. 10/849,301, incorporated by reference in its entirety. Carbene compounds include small molecules, dendrimers, and polymers that include a carbene-metal bond. As used herein, the term "carbene" refers to compounds having a divalent carbon atom with only six electrons in its valence shell when not coordinated to a metal. A useful exercise to determine whether a ligand includes a carbene-metal bond is to mentally deconstruct the complex as a metal fragment and a ligand, and to then determine whether a carbon atom in the ligand that was previously bound to the metal is a neutral divalent carbon atom in the deconstructed state. The resonance forms of a preferred embodiment may be shown as:

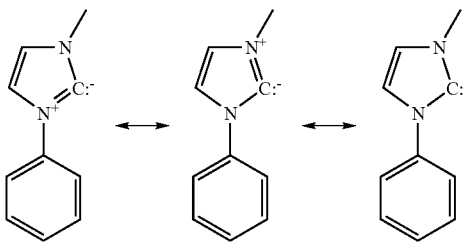

This definition of carbene is not limited to metal-carbene complexes synthesized from carbenes, but is rather intended to address the orbital structure and electron distribution associated with the carbon atom that is bound to the metal. The definition recognizes that the "carbene" may not technically be divalent when bound to the metal, but it would be divalent if it were detached from the metal. Although many such compounds are synthesized by first synthesizing a carbene and then binding it to a metal, the definition is intended to encompass compounds synthesized by other methods that have a similar orbital structure and electron configuration. Lowry & Richardson, *Mechanism and Theory in Organic Chemistry* 256 (Harper & Row, 1976) defines "carbene" in a way that is consistent with the way the term is used herein. Some references may define "carbene" as a carbon ligand that forms a double bond to a metal. While this definition is not being used in the present application, there may be some overlap between the two definitions. A variety of representations are used to depict the bonding in such carbenes, including those in which a curved line is used to indicate partial multiple bonding between the carbene carbon and the adjacent heteroatom(s).

In the figures and structures herein, a carbene-metal bond may be depicted as C→M, as for example:

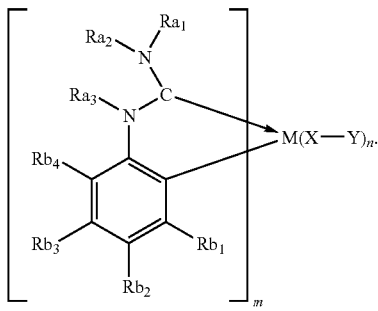

Such structures that use an arrow to represent the presence of a metal-carbene bond are used interchangeably herein with structures that do not include the arrow, without any intention of suggesting there is a difference in the structure shown.

In one embodiment, the invention provides an organic light emitting device, comprising an anode, a cathode, and a phosphorescent emissive region disposed between the anode and the cathode, wherein the emissive region comprises an emissive material having the structure V:

V wherein M is a metal; W, X, Y, and Z are independently a group containing C, N, P, O, or S coordinated to the metal M; and wherein at least one of W, X, Y, or Z is coordinated to the metal by a carbene donor. W, X, Y, and Z are linked to one another by linking groups $L^1$, $L^2$, $L^3$, and optionally $L^4$ (x can be 0 or 1).

In a further embodiment, the emissive material has the structure VI:

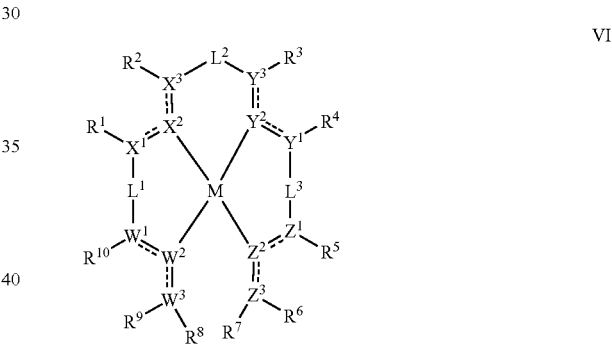

VI wherein:
M is a metal;
the dotted lines represent optional double bonds;
$W^1$, $W^3$, $X^1$, $X^3$, $Y^1$, $Y^3$, $Z^1$, and $Z^3$ are independently C or N;
$W^2$, $X^2$, $Y^2$, and $Z^2$ are independently C, N, O, S or P; wherein at least one of $W^2$, $X^2$, $Y^2$ and $Z^2$ is a carbene;
wherein for each group W, X, Y, and Z at least one of atoms 1, 2, and 3 is C;
$L^1$, $L^2$, and $L^3$ are independently a linking group;
$R^7$ and $R^8$ may optionally be joined to form a linking group $L^4$;
$R^{1-10}$ are independently H, alkyl, alkenyl, alkynyl, heteroalkyl, aralkyl, aryl, heteroaryl, C(O)R', C(O)OR', or C(O)NR'$_2$;
each of $R^1$ and $R^2$, $R^3$ and $R^4$, $R^5$ and $R^6$, and $R^9$ and $R^{10}$, taken together with the atoms of groups X, Y, Z, and W, respectively, can independently and optionally can form a 5- or 6-member cyclic group or an 8- to 10-membered fused bicyclic group, which may be optionally substituted by one or more substituents J;

each substituent J is independently R', O—R', N(R')$_2$, SR', C(O)R', C(O)OR', C(O)NR'$_2$, CN, CF$_3$, NO$_2$, SO$_2$, SOR', SO$_3$R', or halo, and any two J groups on adjacent ring atoms can optionally form a 5- or 6-member cyclic group; and each R' is independently H, alkyl, alkenyl, alkynyl, heteroalkyl, aralkyl, aryl, or heteroaryl.

In this embodiment, in each group W, X, Y, and Z, at least one of atoms 1, 2, and 3 is C. That is, at least one of $W^1$, $W^2$, and $W^3$ is C. Similarly, at least one of $X^1$, $X^2$, and $X^3$ is C. Groups Y and Z are likewise defined.

In a preferred embodiment of structure VI, $R^7$ and $R^8$ are joined to form a linking group $L^4$ to give a macrocyclic compound having the structure VII:

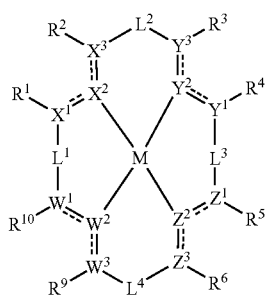

VII wherein $L^4$ is a linking group.

In a further preferred embodiment of structure VI, $R^1$ and $R^2$ (taken together with $X^1$, $X^2$, and $X^3$) form a cyclic group denoted ring A, and $R^3$ and $R^4$ (taken together with $Y^1$, $Y^2$, and $Y^3$) form a cyclic group denoted ring B to give a compound having the structure VIII:

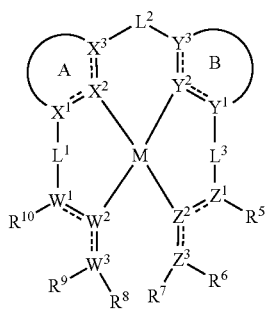

VIII wherein A and B are independently a 5- or 6-membered cyclic group or a 8- to 10-membered fused bicyclic group, which may be optionally substituted with one or more substituents J.

In a further preferred embodiment of structure VIII, $R^5$ and $R^6$ (taken together $Z^1$, $Z^2$, and $Z^3$) form a cyclic group denoted ring C, and $R^9$ and $R^{10}$ (taken together $W^1$, $W^2$, and $W^3$) form a cyclic group denoted ring D, to give a compound having the structure IX:

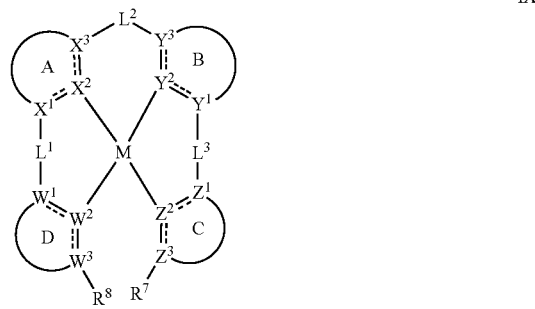

IX wherein A, B, C, and D are independently a 5- or 6-membered cyclic group or a 8- to 10-membered fused bicyclic group, which may be optionally substituted with one or more substituents J.

In a further preferred embodiment of structure IX, $R^7$ and $R^8$ are joined to form a linking group $L^4$ to give a compound having the structure X:

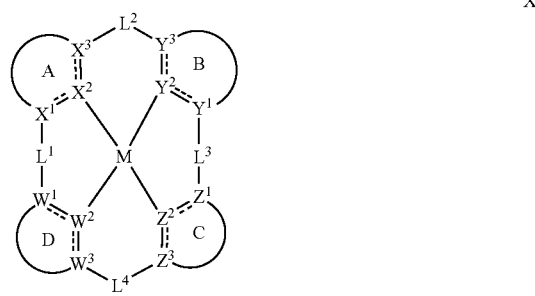

X wherein $L^4$ is a linking group.

In preferred embodiments of structures IX and X, all of the rings A, B, C, and D are aromatic rings. In an especially preferred embodiment, two of the rings A, B, C, and D are imidazole rings, and each of the remaining two rings is a phenyl ring or a pyridyl ring. Accordingly, in one embodiment, the emissive material is a compound having the structure XI:

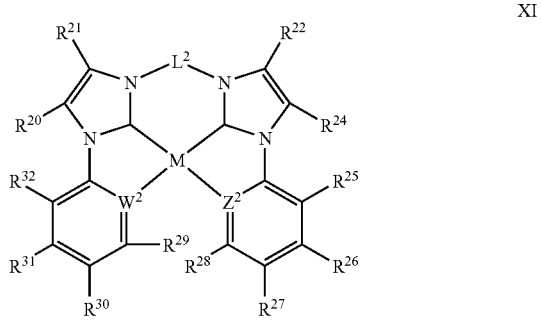

XI wherein:
$W^2$ and $Z^2$ are independently C or N;
$L^2$ is a linking group;
$R^{28}$ and $R^{29}$ may optionally be joined to form a linking group $L^4$;
$R^{20-32}$ are independently a substituent J.

In a preferred embodiment of structure XI, $R^{28}$ and $R^{29}$ are joined to form a linking group $L^4$ to give a compound having the structure XII:

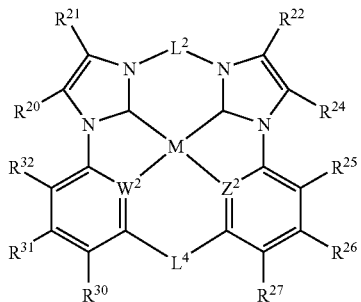

XII wherein $L^4$ is a linking group.

In a further embodiment of the invention, the emissive material is a compound having the structure XIII:

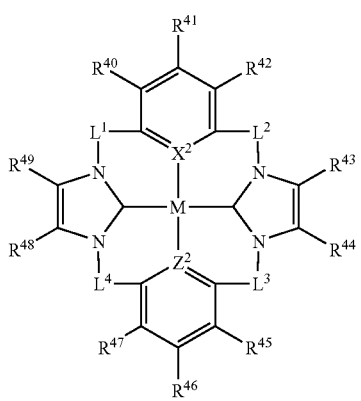

XIII wherein:

$X^2$ and $Z^2$ are independently C or N;

$L^1$, $L^2$, $L^3$, and $L^4$ are independently a linking group;

$R^{40-49}$ are independently a substituent J.

In a preferred embodiment, the compounds according to structures V-XIII are neutral compounds. Neutral compound may have the advantage of being easier to process in the manufacture of the device as they may be deposited using sublimation techniques. In the case where the compound according to structures V-XIII is a charged compound, the compound will include a counterion to balance the charge. The counterion may be selected from any appropriate ion which does not interfere with the function of the compound as an emissive material.

In another embodiment of the invention, the metal-carbene complex will be cationic. Such complexes will have as positive charge ranging from 1+ to 6+, and preferably from 1+ to 2+. The cationic metal-carbene complex will be associated with a weakly coordinating anion to balance the charge. The weakly coordinating anion may be selected from any appropriate anion which does not interfere with the function of the compound in the device, for example, as an emissive material. The weakly coordinating anion is selected to be electrochemically inert over the operational voltage range of the device. The term "weakly coordinating anion" is well known in the art per se and generally refers to a large bulky anion capable of delocalization of the negative change of the anion. Suitable weakly coordinating anions, not all of which would be considered bulky, include, but are not limited to: $PF_6^-$, $BF_4^-$, $SbCl_6^-$, $SbF_6^-$, $(Ph)_4B^-$ wherein Ph=phenyl, $Ar_4B^-$ wherein $Ar=C_6F_5$, $Ar'_4B^-$ wherein Ar'=3,5-bis(trifluoromethyl)phenyl, sulfonates, and the like. The weakly coordinating nature of such anions is known to those skilled in the art and described in the literature (S. Strauss et al., Chem. Rev., 1993, 93, 927).

In some embodiments, the present invention comprises a compound further comprising one or more carbene atoms coordinated to a $d^8$ metal. Preferred metals for this embodiment include Pt(II), Pd(II), Ir(I), Au(III), or Rh(I). Most preferably, the metal is Pt(II).

In one embodiment, the metal is coordinated to one or more carbene donors; 0-3 neutral donors; and 0-3 monoanionic donors; wherein the total number of donors is the maximum number of ligands that may be attached to the metal, and wherein each donor is optionally linked to one or more adjacent donors. In this embodiment, a donor is a group coordinated to the metal. Each donor may be optionally substituted with one or more substituents J.

In one preferred embodiment, the donors are linked to form a macrocyclic ligand. In another preferred embodiment, the macrocyclic ligand is planar. In another preferred embodiment, the metal is coordinated to 4 donors, and the donors are linked to form a tetradentate ligand.

In preferred embodiments, the carbene compounds of the present invention are emissive. In one embodiment, the metal forms a carbon-metal bond with at least one carbon atom that is not a carbene donor. In a preferred embodiment, the metal forms a carbon metal bond with a phenyl group, as it is believed that this type of bonding promotes relaxation, which may result in better emissive properties. In an especially preferred embodiment, the metal is coordinated to two carbene donors and two phenyl groups.

In one embodiment, the metal is coordinated to two bidentate ligands. In another embodiment, the metal is coordinated to one tridentate ligand and one monodentate ligand. In another embodiment, the metal is coordinated to a tetradentate ligand.

Exemplary carbene donors include, but are not limited to:

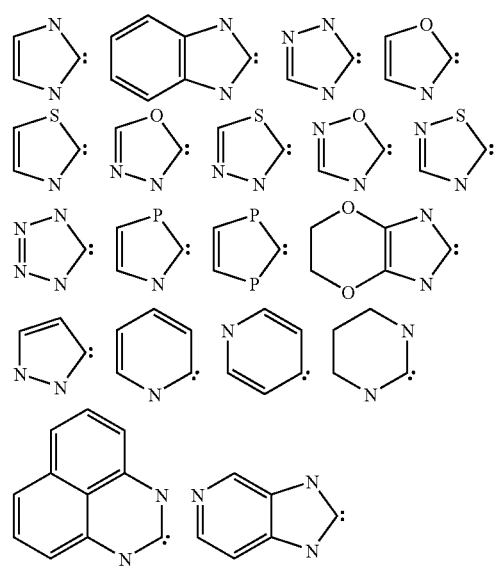

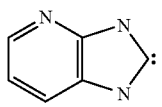
Exemplary monoanionic donors include, but are not limited to:
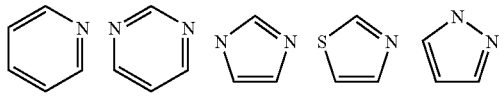
Exemplary monoanionic donors include, but are not limited to:
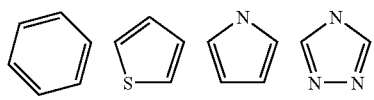
Preferred carbene compounds of the present invention include:
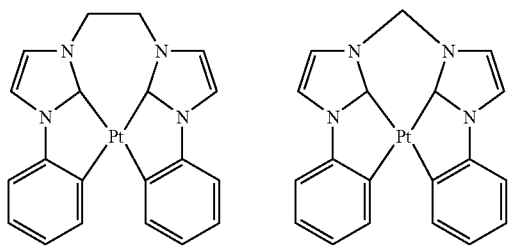
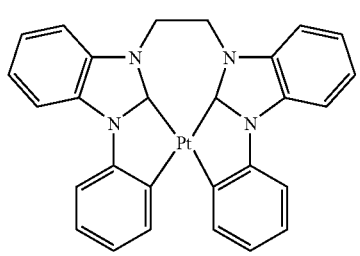
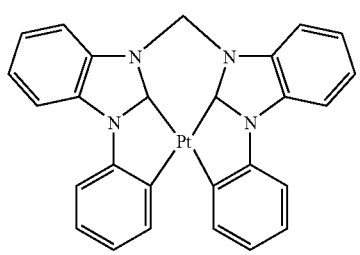
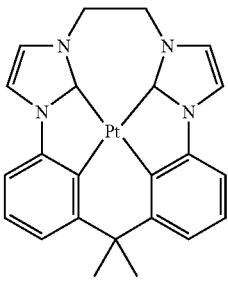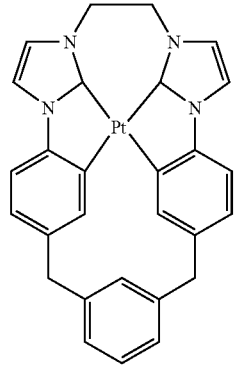
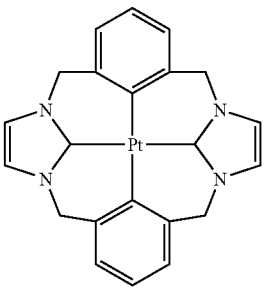
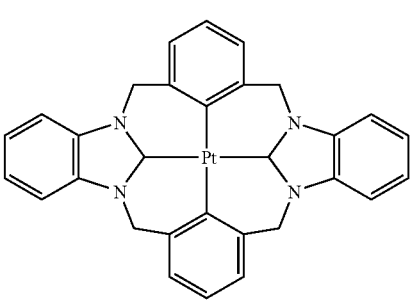
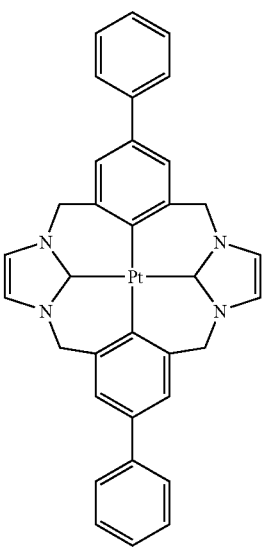

-continued
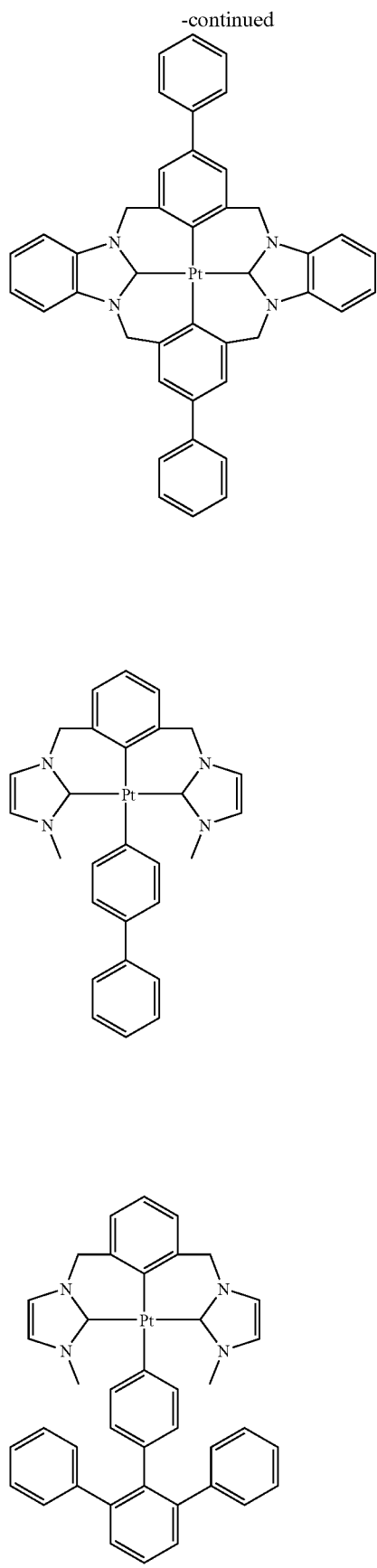
-continued
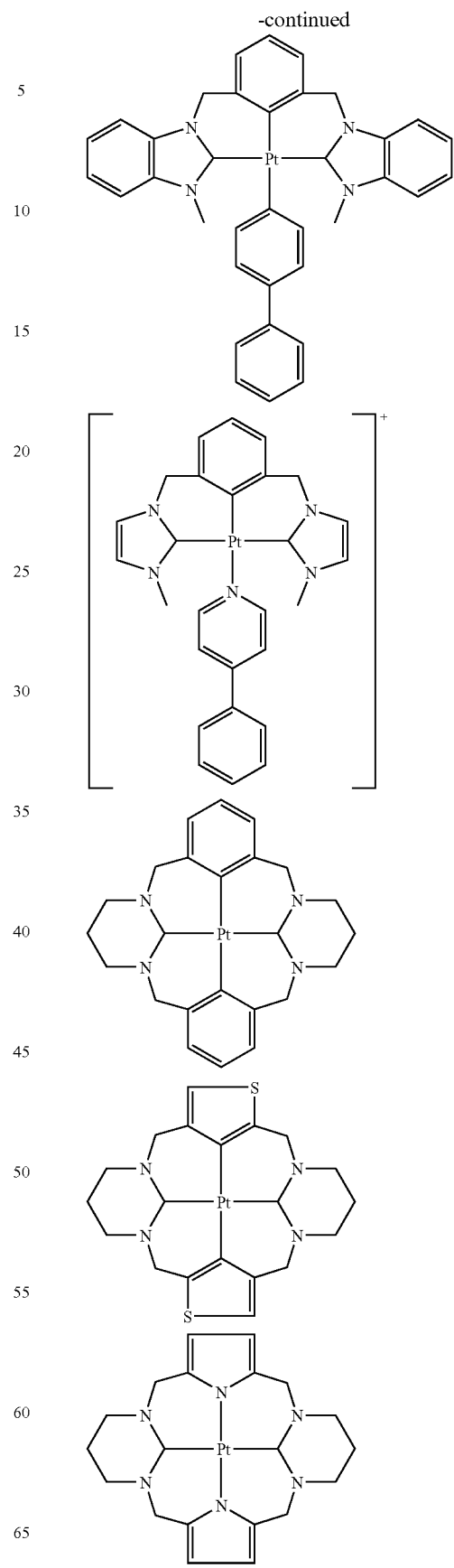

-continued

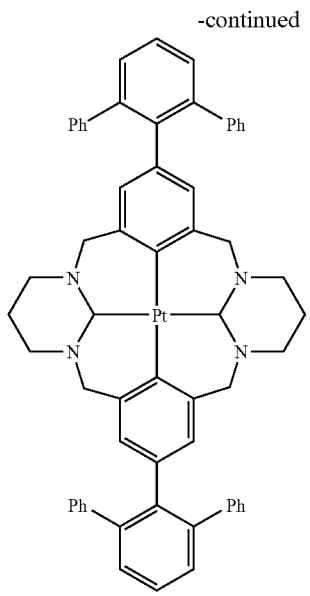

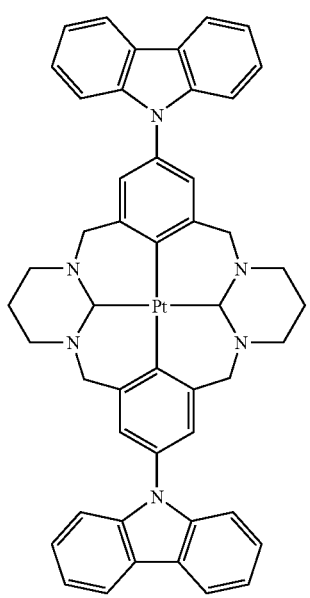

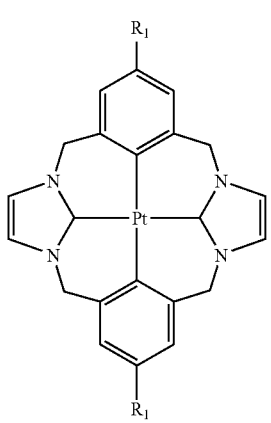

-continued

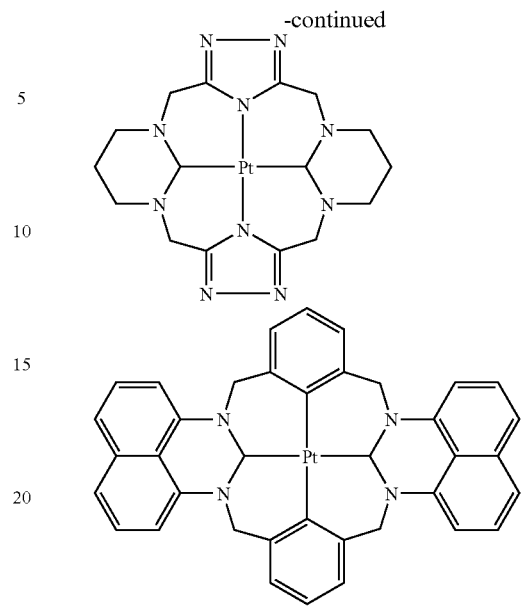

In embodiments of the invention in which the metal is selected to be a metal that preferably adopts an octahedral coordination sphere (for example, Ir, Os, Rh, Ru, etc.), the axial coordination sites may be occupied by monodentate ancillary ligands. An embodiment of such a compound is provided below:

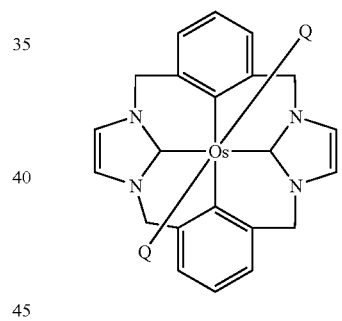

wherein each Q is independently selected from monodentate ancillary ligands.

In some embodiments, the ligands of the present invention emit blue light, that is, the emission has CIE coordinates in the range that corresponds to saturated blue. Blue emission can be achieved by tuning the ligands. Tuning can be accomplished by altering the size of the pi system and/or adding electron donating or accepting groups. Although wavelength depends on the line width, one preferred embodiment comprises at least one ligand that has a triplet energy corresponding to a wavelength of less than 450 nm. If a small line width is achieved, for example, 40 nm or less, wavelengths longer than 450 nm would still emit the preferred saturated blue.

Like other ligand complexes used in OLEDs, planar macrocyclic ligands may show aggregation effects at moderate doping levels. This aggregation effect will lead to combined monomer and excimer/dimer emission at intermediate concentrations, and predominate excimer/dimer emission at high concentration. Monomer only emission is expected at low doping levels, but at the cost of lower efficiency. To reduce aggregation effects, sterically bulky groups may be added to the periphery of the macrocyclic ligands of the present invention. Sterically bulky groups include, but are not limited to, tertiary butyl or mesityl groups. The addition of sterically bulky groups allows for high efficiency OLEDs by allowing emission from the monomer state at high doping levels.

The emissive materials of the present invention comprise at least one photoactive ligand. This ligand is referred to as "photoactive" because it is believed that it contributes to the photoactive properties of the emissive material. A "photoactive" ligand may provide, in conjunction with the metal, the energy levels from which and to which an electron moves when a photon is emitted. Other ligands may be referred to as "ancillary." Ancillary ligands may modify the photoactive properties of the molecule, for example by shifting the energy levels of a photoactive ligands, but ancillary ligands do not directly provide the energy levels involved in light emission. A ligand that is photoactive in one molecule may be ancillary in another. These definitions of photoactive and ancillary are intended as non-limiting theories.

The number of photoactive ligands may be any integer up to the maximum number of ligands that may be attached to the metal. For example, for Ir the maximum number of bidentate ligands bound to the metal would 3, at least one of which would be a photoactive ligand. When more that one photoactive ligand is present, each photoactive ligand may be the same or may be different.

The molecules disclosed herein may be substituted in a number of different ways without departing from the scope of the invention. For example, substituents may be added to a compound having three bidentate ligands, such that after the substituents are added, one or more of the bidentate ligands are linked together to form, for example, a tetradentate or hexadentate ligand. Other such linkages may be formed. It is believed that the metal complexes with multidentate ligands may have improved chemical, thermochemical, electrochemical and photochemical stability compared to the traditional bidentate ligand analogs. As would be understood by those of skill in the art, the improvement in stability may be attributed, at least in part, to what is known as the "chelate effect" such as described in *Inorganic Chemistry* (2nd Edition), Gary L. Miessler, Donald A. Tarr (Prentice Hall, 1998) pp 396-397. Linking two or more ligands to one another may render the resulting ligand system less labile than the corresponding non-linked ligands. As indicated in the mass spectroscopy (EI, 70 eV) of Dopant F (described herein below), for example, there is no fragmentation of the molecular ion whereas significant fragmentation is observed in $Ir(ppy)_3$.

It is believed that the metal complexes with multidentate ligands can have increased photoluminescence quantum yields compared to the traditional bidentate ligand analogs because the complexes with multidentate ligands are more rigid, i.e., with decreased vibrational and rotational freedom, which can be pathways for non-radiative decay.

In metal-ligand complexes, structural isomers may result from the synthesis. For example, in Ir(phenylpyridine)$_3$ type complexes, both facial and meridional isomers can form. Separation of these isomers may be difficult. Through suitable interlinking of the ligands, selective structural isomeric configuration can be achieved. This can significantly improve the synthesis yield and simplify the purification process.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tertbutyl, and the like. Additionally, the alkyl group may be optionally substituted with one or more substituents selected from halo, CN, $CO_2R$, $C(O)R$, $NR_2$, cyclic-amino, $NO_2$, and OR, wherein each R is independently selected from H, alkyl, alkenyl, alkynyl, aralkyl, aryl and heteroaryl.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, $C(O)R$, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, $C(O)R$, $NR_2$, cyclic-amino, $NO_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, $C(O)R$, $NR_2$, cyclic-amino, $NO_2$, and OR.

The term "aralkyl" as used herein contemplates an alkyl group which has as a substituent an aromatic group. Additionally, the aralkyl group may be optionally substituted on the aryl with one or more substituents selected from halo, CN, $CO_2R$, $C(O)R$, $NR_2$, cyclic-amino, $NO_2$, and OR.

The term "heterocyclic group" as used herein contemplates non-aromatic cyclic radicals. Preferred heterocyclic groups are those containing 5 or 6 ring atoms which includes at least one hetero atom, and includes cyclic amines such as morpholino, piperdino, pyrrolidino, and the like, and cyclic ethers, such as tetrahydrofuran, tetrahydropyran, and the like.

The term "aryl" or "aromatic group" as used herein contemplates single-ring aromatic groups (for example, phenyl, pyridyl, pyrazole, etc.) and polycyclic ring systems (naphthyl, quinoline, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles, and/or heteroaryls.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine, pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

Material Definitions:
As used herein, abbreviations refer to materials as follows:

| | |
|---|---|
| CBP: | 4,4'-N,N-dicarbazolebiphenyl |
| m-MTDATA: | 4,4',4''-tris(3-methylphenylphenlyamino)triphenylamine |
| Alq$_3$: | 8-tris-hydroxyquinoline aluminum |
| Bphen: | 4,7-diphenyl-1,10-phenanthroline |
| n-BPhen: | n-doped BPhen (doped with lithium) |
| F$_4$-TCNQ: | tetrafluoro-tetracyano-quinodimethane |
| p-MTDATA: | p-doped m-MTDATA (doped with F$_4$-TCNQ) |
| Ir(ppy)$_3$: | tris(2-phenylpyridine)-iridium |
| Ir(ppz)$_3$: | tris(1-phenylpyrazoloto,N,C(2')iridium(III) |
| BCP: | 2,9-dimethyl-4,7-diphenyl-1,10-phenanthroline |
| TAZ: | 3-phenyl-4-(1'-naphthyl)-5-phenyl-1,2,4-triazole |
| CuPc: | copper phthalocyanine. |
| ITO: | indium tin oxide |
| NPD: | N,N'-diphenyl-N-N'-di(1-naphthyl)-benzidine |
| TPD: | N,N'-diphenyl-N-N'-di(3-toly)-benzidine |
| BAlq: | aluminum(III)bis(2-methyl-8-hydroxyquinolinato)4-phenylphenolate |
| mCP: | 1,3-N,N-dicarbazole-benzene |
| DCM: | 4-(dicyanoethylene)-6-(4-dimethylaminostyryl-2-methyl)-4H-pyran |
| DMQA: | N,N'-dimethylquinacridone |
| PEDOT: PSS: | an aqueous dispersion of poly(3,4-ethylenedioxythiophene) with polystyrenesulfonate (PSS) |
| Ir(4,6-F$_2$ppy)$_3$: | tris[2-(4,6-difluorophenyl)pyridine]iridium(III) |
| mCP: | 3,5-N,N'-dicarbazolebenzene |

EXPERIMENTAL

Specific representative embodiments of the invention will now be described, including how such embodiments may be made. It is understood that the specific methods, materials, conditions, process parameters, apparatus and the like do not necessarily limit the scope of the invention.

Where available, solvents and reagents were purchased from Aldrich Chemical Company. The reagents were of the highest purity and used as received.

Example 1

Synthesis of Pt152

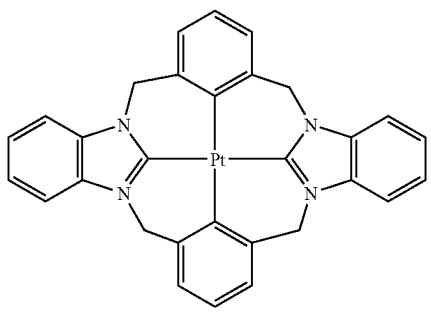

Pt152

Step 1: Synthesis of 1-[3-(1H-benzimidazole-1yl-methyl)benzyl]-1H-benzimidazole

To a 1L round bottom flask equipped with a stirbar was added 26.8 g benzimidazole (227 mmol) and 12.7 g (227 mmol) finely pulverized potassium hydroxide. These were stirred in 500 mL acetone for 20 minutes at reflux. 20.0 g (78.5 mmol) α,α'-dibromo-m-xylene was then added, and the solution was stirred at reflux for 6 hours followed by room temperature stirring for 72 hours. The cloudy solution was filtered, and the white solids rinsed with acetone. The resulting filtrate was dried on silica and partitioned on a silica gel column using a gradient of 100% acetonitrile→90% acetonitrile/10% MeOH as eluent. The product fractions were evaporated of solvent to give 5 g 1-[3-(1H-benzimidazole-1yl-methyl)benzyl]-1H-benzimidazole as a white solid.

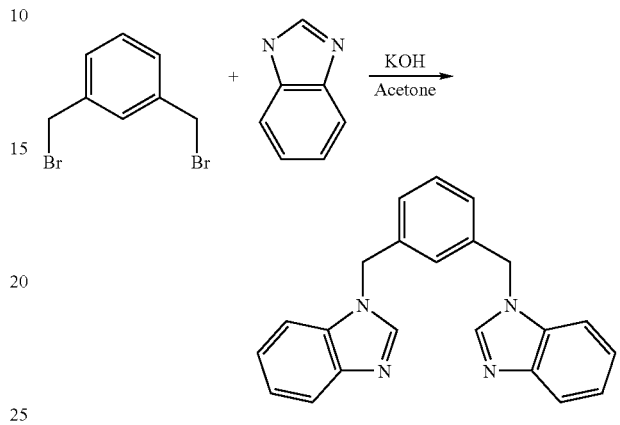

Step 2: Synthesis of 1-bromo-α,α'-dibromo-m-xylene

To a 1L flask charged with 300 mL carbon tetrachloride was added 50.0 g (270 mmol) 1-bromo-2,6-diemthylbenzene and 100.9 g (567 mmol) N-bromosuccinimide. As this solution was stirred, 200 mg benzoyl peroxide was added, and the mixture was allowed to reflux for 30 minutes. Afterwards, the mixture was cooled, and an additional 200 mg benzoyl peroxide was added and then reheated to reflux for an additional 30 minutes. This process was repeated two more times, and then the mixture was allowed to reflux for 20 hours. Finally, the solution was allowed to cool and then was filtered. Evaporation of the filtrate gave a waxy brown solid that was recrystallized from cyclohexane, filtered, rinsed with hexanes, and dried to give ~20 g 1-bromo-2,6-dibromo-m-xylene as a white powder.

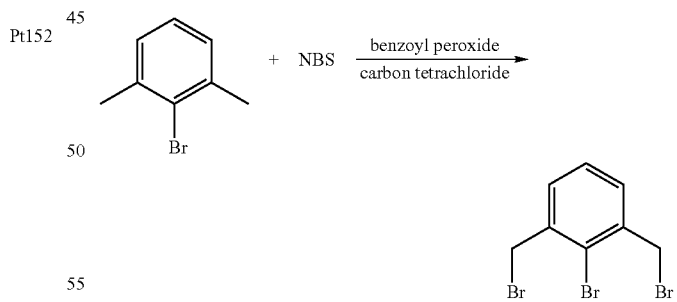

Step 3: Synthesis of Benzimidazoliophane-Br

In a 250 mL flask, 2.0 g (5.91 mmol) 1-[3-(1H-benzimidazole-1yl-methyl)benzyl]-1H-benzimidazole was solubilized in 100 mL acetone with stirring action. 2.03 g (5.91 mmol) 1-bromo-α,α'-dibromo-m-xylene dissolved in 60 mL acetone was then added dropwise. After addition, the mixture refluxed for 20 hours whereupon white solids developed. The mixture was then cooled, filtered, and the benzimidazoliophane-Br rinsed with acetone to give 3.3 g as a white solid.

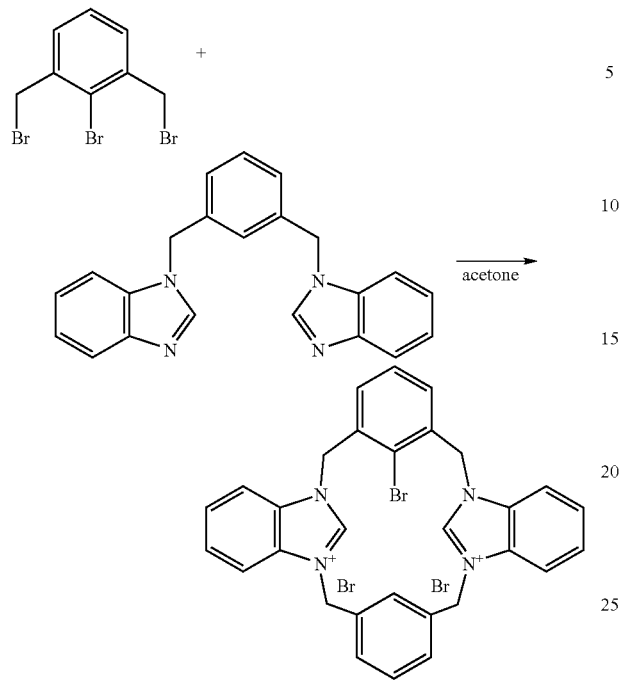

Step 4: Synthesis of Pt (II) benzimidazoliophane (Pt152)

In a 250 mL three neck flask, 100 mL 2-methoxyethanol was thoroughly degassed (2 hours) with $N_2$ and heat. The solvent was then cooled to 70° C. whereupon 1.83 g (1.47 mmol) tetrakistriphenylphosphine platinum (0), 1.00 g (4.02 mmol) benzimidazoliophane-Br and 0.81 g (5.87 mmol) potassium carbonate were added. The mixture was set to reflux for 30 minutes and then immediately cooled. The solution was filtered warm to remove unsolubilized base. Finally, the filtrate was evaporated to 15 mL and enriched with 200 mL methanol to precipitate the product. Filtration of this solution gave yellow solids that were dissolved in methylene chloride and purified on a thin silica gel column using methylene chloride as eluent. Removal of solvent and recrystallization from methylene chloride/methanol gave ~0.15 g Pt (II) benzimidazoliophane as a yellow solid as confirmed by NMR ($\lambda_{max}$=535 nm (DMF), Ox: 0.72(i) vs. ferrocene, Red: not detectable).

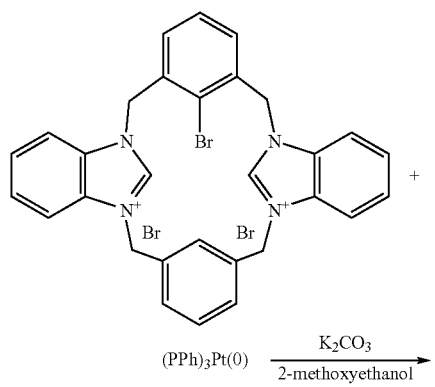

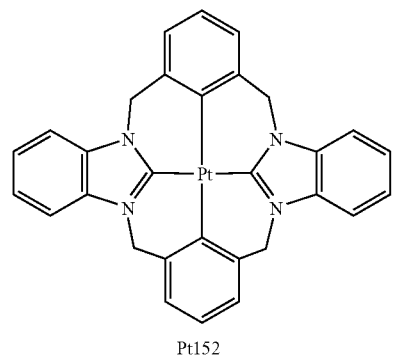

Pt152

Example 2

Synthesis of Pt151

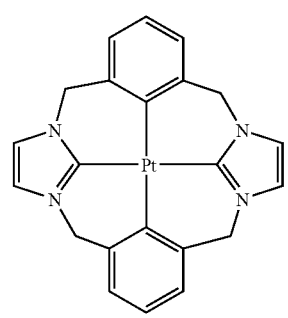

Pt151

Step 1: Synthesis of 1-[3-(1H-imidazole-1yl-methyl)benzyl]-1H-imidazole

To a 500 mL round bottom flask equipped with a stirbar was added 11.6 g imidazole (170 mmol) and 9.55 g (170 mmol) finely pulverized potassium hydroxide. These were stirred in 200 mL acetone until the solution became yellow translucent. 15.0 g (56.8 mmol) α,α'-dibromo-m-xylene was then added, and the solution was stirred at room temperature overnight. The cloudy solution was filtered, and the white solids rinsed with acetone. The resulting filtrate was dried on silica and partitioned on a silica gel column using 30/70 acetonitrile/methanol as eluent. The product fractions were evaporated of solvent and the resulting oil recrystallized from ethyl acetate/hexanes to give 8.65 g 1-[3-(1H-imidazole-1yl-methyl)benzyl]-1H-imidazole as a white solid.

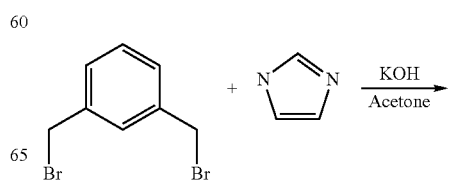

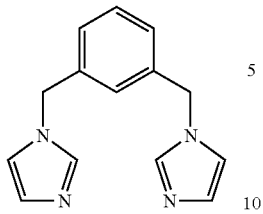

Step 2: Synthesis of 1-bromo-α;α'-dibromo-m-xylene

To a 1L flask charged with 150 mL chlorobenzene was added 24.7 g (134 mmol)1-bromo-2,6-diemthylbenzene and 48.3 g (271 mmol) N-bromosuccinimide. As this solution was stirred, 1.12 g benzoyl peroxide (4.6 mmol) was added and the mixture was allowed to reflux 1 hour (Caution: as the reaction mixture began to heat, a violent exotherm occurred whereby the reaction contents shot up the condenser. It is possible that the mixture could evolve from the condenser for any given reaction). An additional 0.75 g benzoyl peroxide was then added, and the mixture was refluxed for an additional 4 hours. Finally, the solution was allowed to cool to room temperature and stirred overnight. This solution was filtered, and the solids rinsed with chlorobenzene. Evaporation of the solvent gave a waxy brown solid that was distilled twice via Kugelrohr to remove impurities. The solids were then recrystallized from methanol to give ~15 g 1-bromo-2,6-dibromo-m-xylene as a white powder.

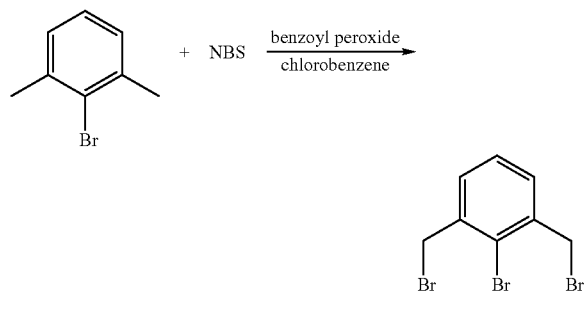

Step 3: Synthesis of Imidazoliophane-Br

In a 1L flask, 8.31 g (34.9 mmol) 1-[3-(1H-imidazole-1yl-methyl)benzyl]-1H-imidazole was solubilized in 400 mL acetone with stirring action. 12.0 g (34.9 mmol) 1-bromo-α,α'-dibromo-m-xylene dissolved in 150 mL acetone was then added dropwise. After addition, the mixture refluxed for 2 hours whereupon white solids developed. The mixture was then cooled, filtered, and the Imidazoliophane-Br rinsed with acetone. This product was then recrystallized from methanol to give 4.0 g as a white powder. The remaining portion (+10 g) was left as a crude light brown solid.

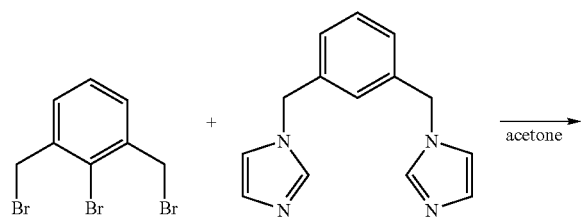

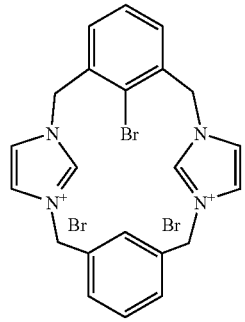

Step 4: Synthesis of Pt (II) imidazoliophane

In a 1L three neck flask, 200 mL 2-methoxyethanol was thoroughly degassed (2 hours) with $N_2$ and heat. The solvent was then cooled to 70° C. whereupon 5.0 g (4.02 mmol) tetrakistriphenylphosphine platinum (0), 2.34 g (4.02 mmol) imidazoliophane-Br and 2.22 g (16.1 mmol) potassium carbonate were added. The mixture was set to reflux for 15 minutes and then immediately cooled. The solution was filtered to give ~0.9 g of white solid. Its filtrate was reduced to 50 mL via evaporation and enriched with 300 mL methanol. Another filtration gave an additional 0.37 g of white solid. These were combined and stirred in a mixture of water/methanol to solubilize any residual base and triphenylphoshine. A final filtration yielded 0.9 g of product. It was purified via high vacuum sublimation to give ~0.7 g Pt (II) imidazoliophane as a white powdery solid as confirmed by MS and NMR ($\lambda_{max}$=486 nm (DMF), Ox: 0.64V (i) vs. ferrocene, Red: not detectable, $T_m$: 491° C., $T_g$: not detectable).

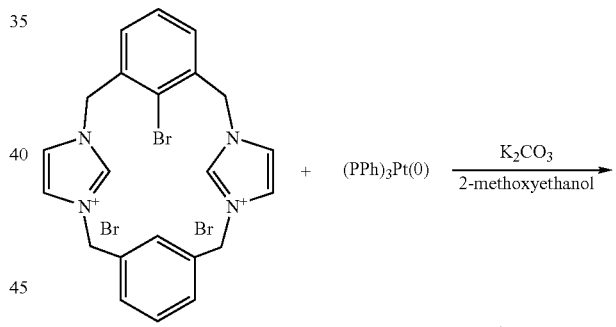

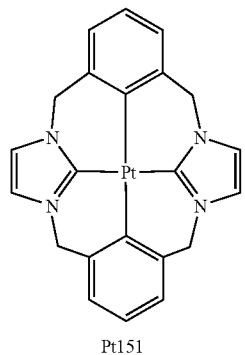

Pt151

What is claimed is:

1. An organic light emitting device, comprising:
   (a) an anode;
   (b) a cathode;
   (c) an organic layer disposed between the anode and the cathode, wherein the organic layer comprises a compound comprising one or more carbene atoms coordinated to a d⁸ metal; wherein the compound further comprises a multidentate ligand.

2. The device of claim 1, wherein the metal is Pt(II), Pd(II), Ir(I), Au(III), or Rh(I).

3. The device of claim 2, wherein the metal is Pt(II).

4. An organic light emitting device, comprising:
(a) an anode;
(b) a cathode;
(c) and a phosphorescent emissive region disposed between the anode and the cathode, wherein the emissive region comprises an emissive material having a structure V:

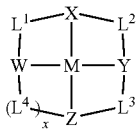

wherein:
M is a metal;
W, X, Y, and Z are independently a group containing C, N, P, O, or S coordinated to the metal M;
at least one of W, X, Y, or Z is coordinated to the metal by a carbene donor;
$L^1$, $L^2$, $L^3$, and $L^4$ are independently a linking group;
x can be 0 or 1.

5. The device of claim 4, wherein the emissive material has a structure VI:

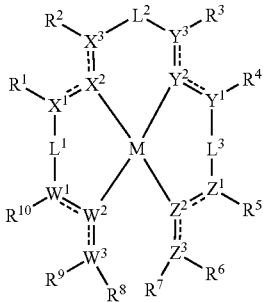

wherein:
M is Pt or Pd;
the dotted lines represent optional double bonds;
$W^1$, $W^3$, $X^1$, $X^3$, $Y^1$, $Y^3$, $Z^1$, and $Z^3$ are independently C or N;
$W^2$, $X^2$, $Y^2$, and $Z^2$ are independently C, N, O, S or P; wherein at least one of $W^2$, $X^2$, $Y^2$ and $Z^2$ is a carbene;
wherein for each group W, X, Y, and Z at least one of atoms 1, 2, and 3 is C;
$L^1$, $L^2$, and $L^3$ are independently a linking group;
$R^7$ and $R^8$ may optionally be joined to form a linking group $L^4$;
$R^{1-10}$ are independently H, alkyl, alkenyl, alkynyl, heteroalkyl, aralkyl, aryl, heteroaryl, C(O)R', C(O)OR', or C(O)NR'$_2$;
each of $R^1$ and $R^2$, $R^3$ and $R^4$, $R^5$ and $R^6$, and $R^9$ and $R^{10}$, taken together with the atoms of groups X, Y, Z, and W, respectively, can independently and optionally form a 5- or 6-member cyclic group or an 8- to 10-membered fused bicyclic group, which may be optionally substituted by one or more substituents J;

each substituent J is independently R', O—R', N(R')$_2$, SR', C(O)R', C(O)OR', C(O)NR'$_2$, CN, CF$_3$, NO$_2$, SO$_2$, SOR', SO$_3$R', or halo, and any two J groups on adjacent ring atoms can optionally form a 5- or 6-member cyclic group; and each R' is independently H, alkyl, alkenyl, alkynyl, heteroalkyl, aralkyl, aryl, or heteroaryl.

6. The device of claim 5, wherein the emissive material has a structure VII:

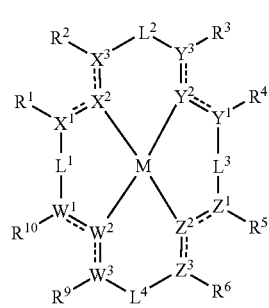

wherein $L^4$ is a linking group.

7. The device of claim 5, wherein the emissive material has a structure VIII:

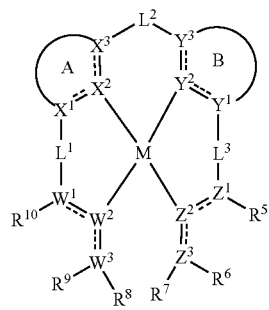

wherein A and B are independently a 5- or 6-membered cyclic group or a 8- to 10-membered fused bicyclic group, which may be optionally substituted with one or more substituents J.

8. The device of claim 7, wherein the emissive material has a structure IX:

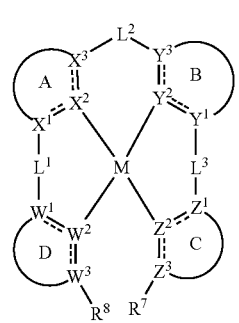

wherein A, B, C, and D are independently a 5- or 6-membered cyclic group or a 8- to 10-membered fused bicyclic group, which may be optionally substituted with one or more substituents J.

9. The device of claim 8, wherein the emissive material has a structure X:

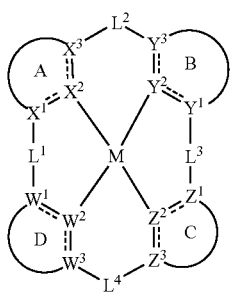

wherein $L^4$ is a linking group.

10. The device of claim 8, wherein all of the rings A, B, C, and D are aromatic rings.

11. The device of claim 8, wherein two of the rings A, B, C, and D are imidazole rings, and each of the remaining two rings is a phenyl ring or a pyridyl ring.

12. The device of claim 11, wherein the emissive material has a structure XI:

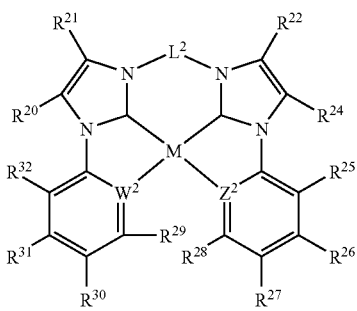

wherein:
$W^2$ and $Z^2$ are independently C or N;
$L^2$ is a linking group;
$R^{28}$ and $R^{29}$ may optionally be joined to form a linking group $L^4$;
$R^{20-22}$ and $R^{24-32}$ are independently a substituent J.

13. The device of claim 12, wherein the emissive material has a structure XII:

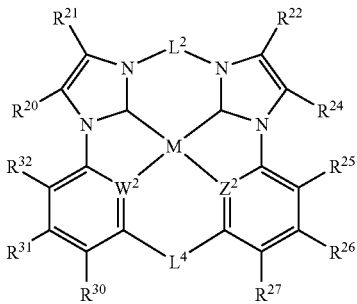

wherein $L^4$ is a linking group.

14. The device of claim 11, wherein the emissive material has a structure XIII:

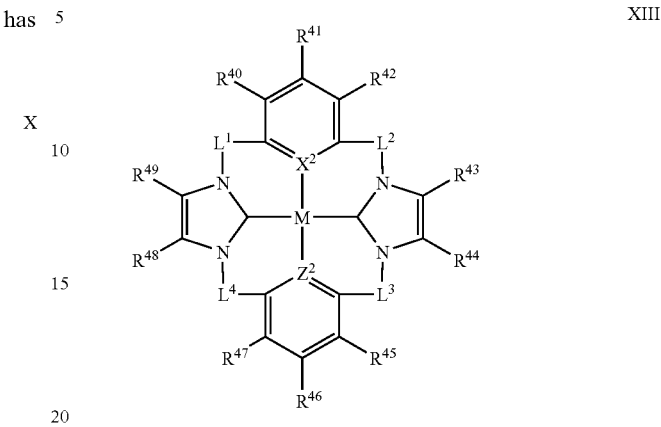

wherein:
$X^2$ and $Z^2$ are independently C or N;
$L^1$, $L^2$, $L^3$, and $L^4$ are independently a linking group;
$R^{40-49}$ are independently a substituent J.

15. An organic light emitting device, comprising:
(a) an anode;
(b) a cathode;
(c) an organic layer disposed between the anode and the cathode, wherein the organic layer comprises a compound comprising a metal coordinated to:
i) one or more carbene donors;
ii) 0-3 neutral donors; and
iii) 0-3 monoanionic donors;
wherein the total number of donors is the maximum number of ligands that may be attached to the metal, and each donor is optionally linked to one or more adjacent donors, and two or more donors are linked to form a macrocyclic ligand.

16. The device of claim 15, wherein each interplanar angle of the macrocyclic ligand is less than about 15°.

17. The device of claim 16, wherein each interplanar angle is less than about 10°.

18. The device of claim 17, wherein each interplanar angle is about 0°.

19. The device of claim 15, wherein the metal is coordinated to 4 donors, and the donors are linked to form a tetradentate ligand.

20. The device of claim 15, wherein the metal is coordinated to:
a) one or more carbene donors, wherein each carbene donor is selected from the group consisting of:

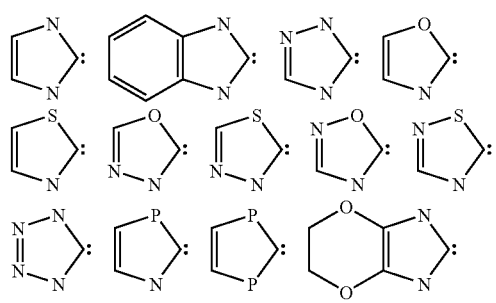

-continued

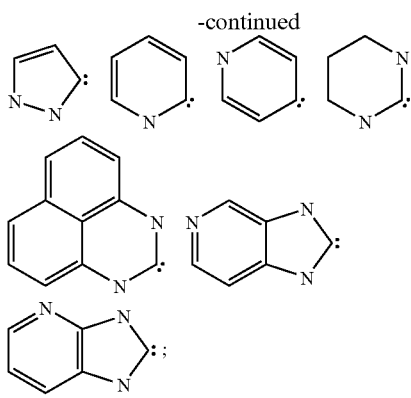

b) 0-3 neutral donors, wherein each neutral donor is selected from the group consisting of:

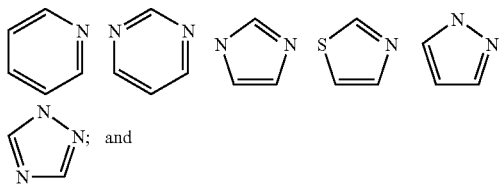

c) 0-3 monoanionic donors, wherein each monoanionic donor is selected from the group consisting of:

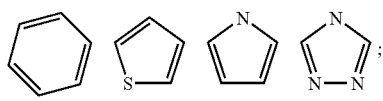

wherein each donor is optionally substituted with one or more substituents J;

each substituent J is independently R', O—R', N(R')$_2$, SR', C(O)R', C(O)OR', C(O)NR'$_2$, CN, NO$_2$, SO$_2$, SOR', or SO$_3$R', and any two J groups on adjacent ring atoms can optionally form a 5- or 6-member aromatic group; and each R' is independently H, alkyl, alkenyl, alkynyl, heteroalkyl, aralkyl, aryl, or heteroaryl.

21. The device of claim 20, wherein the metal forms a carbon-metal bond with at least one carbon atom that is not a carbene donor.

22. The device of claim 21, wherein the metal forms a carbon-metal bond with a phenyl group.

23. The device of claim 22, wherein the metal is coordinated to two carbene donors and two phenyl groups.

24. The device of claim 20, wherein the metal is coordinated to two bidentate ligands.

25. The device of claim 20, wherein the metal is coordinated to one tridentate ligand and one monodentate ligand.

26. The device of claim 20, wherein the metal is coordinated to a tetradentate ligand.

27. The device of claim 20, wherein at least one ligand has a triplet energy corresponding to a wavelength of less than 450 nm.

28. The device of claim 20, wherein the compound is selected from the group consisting of:

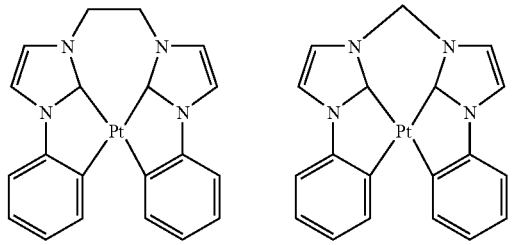

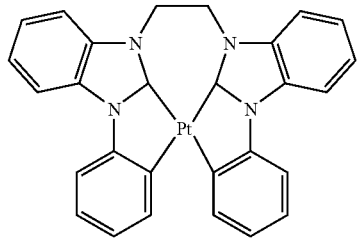

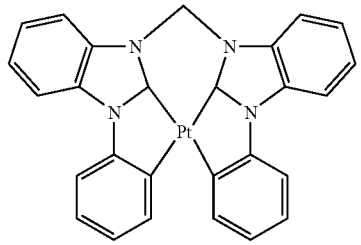

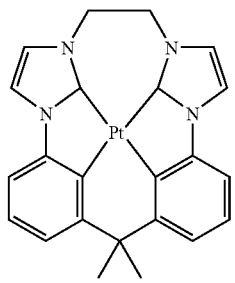
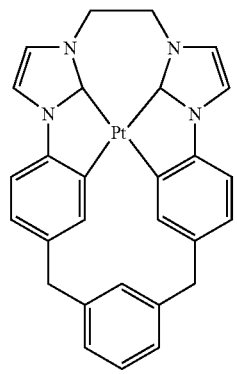

-continued
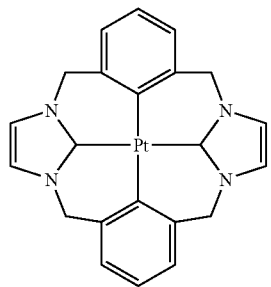
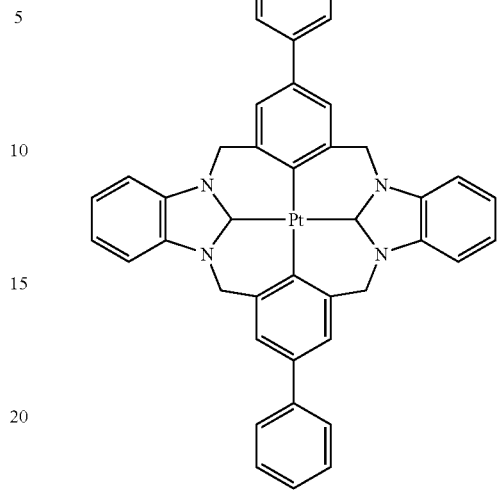
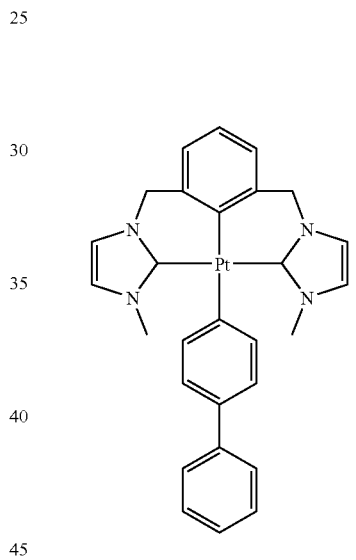
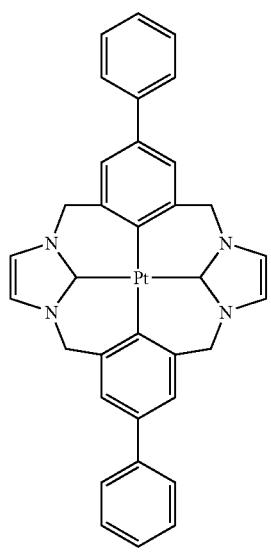
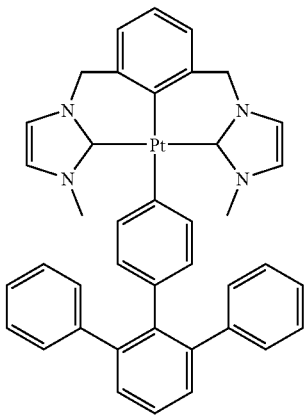

-continued
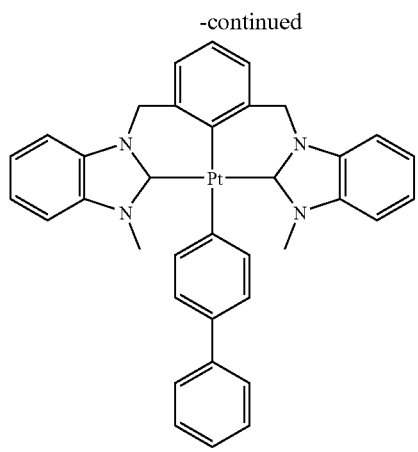
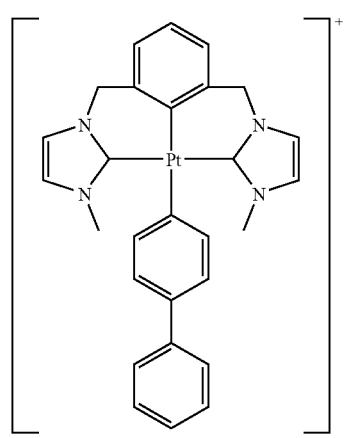
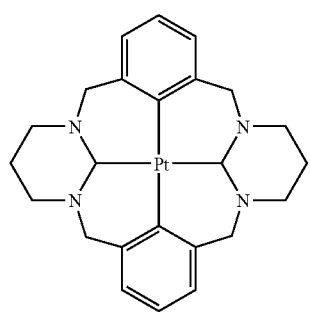
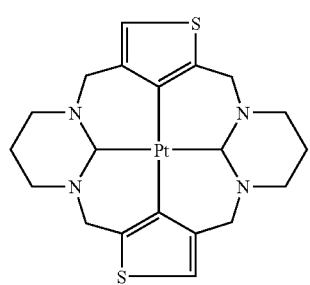
-continued
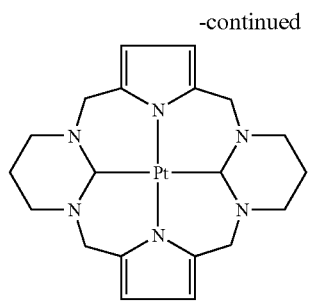
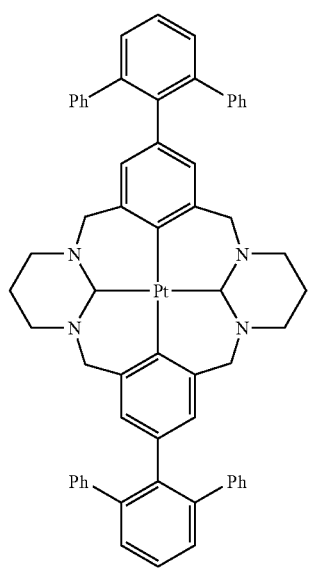
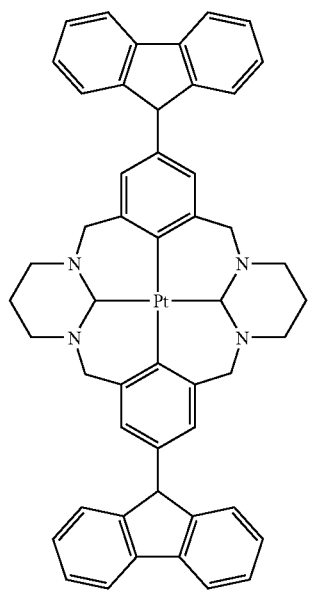

-continued
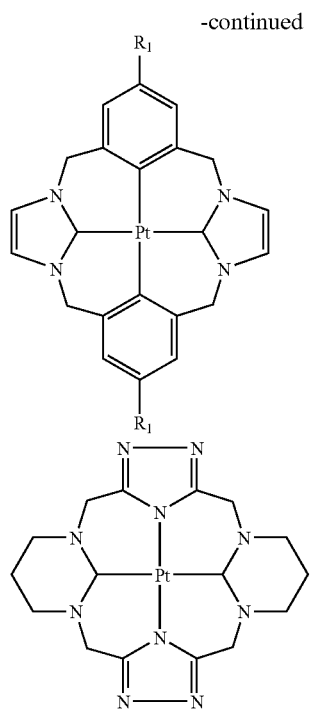
-continued
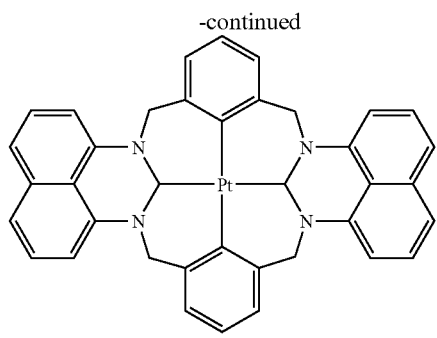
wherein each substituent $R^1$ is independently R', O—R', $N(R')_2$, SR', C(O)R', C(O)OR', $C(O)NR'_2$, CN, $NO_2$, $SO_2$, SOR', or $SO_3R'$, and each R' is independently H, alkyl, alkenyl, alkynyl, heteroalkyl, aralkyl, aryl, or heteroaryl.
* * * * *

UNITED STATES PATENT AND TRADEMARK OFFICE
CERTIFICATE OF CORRECTION

PATENT NO. : 7,655,323 B2
APPLICATION NO. : 11/031078
DATED : February 2, 2010
INVENTOR(S) : Walters et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 816 days.

Signed and Sealed this

Twenty-third Day of November, 2010

David J. Kappos
*Director of the United States Patent and Trademark Office*